(12) United States Patent
Yoshida et al.

(10) Patent No.: US 9,139,419 B2
(45) Date of Patent: *Sep. 22, 2015

(54) RESONANT TRANSDUCER, MANUFACTURING METHOD THEREFOR, AND MULTI-LAYER STRUCTURE FOR RESONANT TRANSDUCER

(71) Applicant: YOKOGAWA ELECTRIC CORPORATION, Musashino-shi, Tokyo (JP)

(72) Inventors: Takashi Yoshida, Musashino (JP); Shuuji Okuda, Musashino (JP); Shigeto Iwai, Musashino (JP)

(73) Assignee: YOKOGAWA ELECTRIC CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/336,613

(22) Filed: Jul. 21, 2014

(65) Prior Publication Data

US 2015/0028434 A1    Jan. 29, 2015

(30) Foreign Application Priority Data

Jul. 24, 2013    (JP) ................. 2013-153874

(51) Int. Cl.
*H01L 29/84*    (2006.01)
*B81B 3/00*    (2006.01)
(Continued)

(52) U.S. Cl.
CPC ............. *B81B 3/0021* (2013.01); *B81B 3/0002* (2013.01); *B81B 7/02* (2013.01);
(Continued)

(58) Field of Classification Search
CPC ............... B81B 2201/0271; B81B 2201/0285; B81B 3/0002; B81B 3/0021; B81B 7/02; B81C 1/00198; G01L 1/14; G01N 2291/014; G01N 2291/02827; G01N 29/12; H01L 41/094; H03H 3/0072; H03H 9/2463
USPC ............. 257/415, 416; 310/321; 73/727, 579, 73/704; 361/290
See application file for complete search history.

(56) References Cited

U.S. PATENT DOCUMENTS 5,123,282 A * 6/1992 Ikeda et al. ............... 73/704
5,581,038 A * 12/1996 Lampropoulos et al. ....... 73/727
(Continued)

FOREIGN PATENT DOCUMENTS

EP    1544162 A1    6/2005
EP    2428783 A1    3/2012
(Continued)

*Primary Examiner* — Fernando L Toledo
*Assistant Examiner* — Mohammad Shamsuzzaman
(74) *Attorney, Agent, or Firm* — Sughrue Mion, PLLC

(57) ABSTRACT

A resonant transducer includes a silicon single crystal substrate, a silicon single crystal resonator disposed over the silicon single crystal substrate, a shell made of silicon, surrounding the resonator with a gap, and forming a chamber together with the silicon single crystal substrate, an exciting module configured to excite the resonator, a vibration detecting module configured to detect vibration of the resonator, a first layer disposed over the chamber, the first layer having a through-hole, a second layer disposed over the first layer, a third layer covering the first layer and the second layer, and a projection extending from the second layer toward the resonator, the projection being spatially separated from the resonator, the projection being separated from the first layer by a first gap, the second layer being separated from the first layer by a second gap, the first gap is communicated with the second gap.

6 Claims, 19 Drawing Sheets

(51) Int. Cl.
| | |
|---|---|
| *G01N 29/12* | (2006.01) |
| *H01L 41/09* | (2006.01) |
| *H03H 3/007* | (2006.01) |
| *H03H 9/24* | (2006.01) |
| *B81B 7/02* | (2006.01) |
| *B81C 1/00* | (2006.01) |
| *G01L 1/14* | (2006.01) |

(52) U.S. Cl.
CPC .............. *B81C 1/00198* (2013.01); *G01L 1/14* (2013.01); *G01N 29/12* (2013.01); *H01L 41/094* (2013.01); *H03H 3/0072* (2013.01); *H03H 9/2463* (2013.01); *B81B 2201/0271* (2013.01); *B81B 2201/0285* (2013.01); *G01N 2291/014* (2013.01); *G01N 2291/02827* (2013.01)

(56) References Cited

U.S. PATENT DOCUMENTS

| | | | | |
|---|---|---|---|---|
| 7,277,267 | B1* | 10/2007 | Bonin | 361/290 |
| 8,222,065 | B1 | 7/2012 | Smeys et al. | |
| 8,445,977 | B2* | 5/2013 | Yoshida | 257/416 |
| 2008/0041607 | A1 | 2/2008 | Robert | |
| 2009/0167107 | A1 | 7/2009 | Huang | |
| 2012/0060607 | A1* | 3/2012 | Yoshida | 73/579 |
| 2013/0002244 | A1* | 1/2013 | Quevy | 324/244 |
| 2015/0042208 | A1* | 2/2015 | Yoshida et al. | 310/321 |

FOREIGN PATENT DOCUMENTS

| | | |
|---|---|---|
| FR | 2864340 A1 | 6/2005 |
| JP | 2005-37309 A | 2/2005 |
| JP | 2012-058127 A | 3/2012 |
| WO | 0158804 A2 | 8/2001 |

* cited by examiner

RESONANT TRANSDUCER, MANUFACTURING METHOD THEREFOR, AND MULTI-LAYER STRUCTURE FOR RESONANT TRANSDUCER

BACKGROUND OF THE INVENTION

1. Field of the Invention

The present invention relates to a resonant transducer, a manufacturing method therefor, and a multi-layer structure for a resonant transducer.

Priority is claimed on Japanese Patent Application No. 2013-153874, filed Jul. 24, 2013, the content of which is incorporated herein by reference.

2. Description of Related Art

A resonant transducer has been known as a sensor for detecting physical stress. For example, the resonant transducer includes a vacuum chamber, a microscopic resonator disposed in the chamber, and a vibration detector detecting vibrations of the microscopic resonator. As shown in Japanese Unexamined Patent Application Publication No. 2012-58127, the chamber, the microscopic resonator, and the vibration detector are disposed in a silicon substrate (silicon wafer).

SUMMARY OF THE INVENTION

A manufacturing method of a resonant transducer may include a silicon single crystal substrate, a silicon single crystal resonator disposed over the silicon single crystal substrate, a shell made of silicon, surrounding the resonator with a gap, and forming a chamber together with the silicon single crystal substrate, an exciting module configured to excite the resonator, a vibration detecting module configured to detect vibration of the resonator, a first layer disposed over the chamber, the first layer having a through-hole, a second layer disposed over the first layer, a third layer covering the first layer and the second layer, and a projection extending from the second layer toward the resonator, the projection being spatially separated from the resonator, the projection being separated from the first layer by a first gap, the second layer being separated from the first layer by a second gap, the first gap is communicated with the second gap.

DETAILED DESCRIPTION OF THE INVENTION

Before describing some embodiments, the related art will be explained with reference to one or more drawings, in order to facilitate the understanding of the embodiments.

Figure 30:
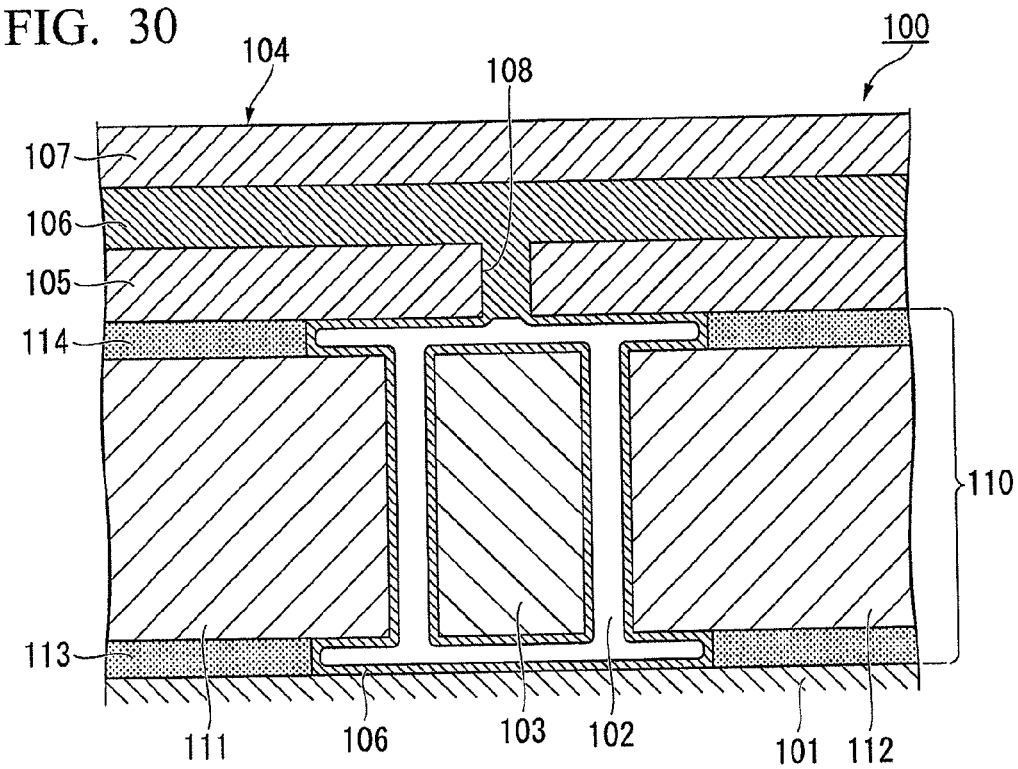
FIG. 30 is an exemplary sectional view illustrating a main part of the resonant transducer in the related art.

FIG. 30 is a drawing showing an example of a resonant transducer 100 in the related art. The resonant transducer 100 shown in FIG. 30 includes a silicon substrate 101 for a measurement diaphragm. The resonant transducer 100 also includes a multi-layer structure 110 over the substrate 101. The multi-layer structure 110 includes oxidized layer 113 and insulated layer 114. The multi-layer structure 110 also includes first electrode 111 and second electrode 112, which are above the oxidized layer 113 and below the insulated layer 114. The first electrode 111 and the second electrode 112 are separated by a chamber 102 in which a resonator 103 is disposed. The resonator 103 is separated by gaps from the first and second electrodes 111 and 112. A shell 104 is disposed on the insulated layer 114 and over the resonator 103, so that the shell 104 seals the chamber 102.

The shell 104 includes a first polysilicon layer (first layer) 105, a second polysilicon layer (second layer) 106, and a third polysilicon layer (third layer) 107. The first polysilicon layer 105 is disposed over the chamber 102. The second polysilicon layer 106 is disposed over the first polysilicon layer 105. The second polysilicon layer 106 has a layer and a plug. The layer extends over the first polysilicon layer 105. The plug is in the first polysilicon layer 105.

For example, a through-hole 108 in the first polysilicon layer 105 is a flow path in which etching liquid flows in a process of forming the chamber 102. After the through-hole 108 is used as a flow path in which etching waste liquid flows, the through-hole 108 is filled up with the plug of the second polysilicon layer 106 with no space in the through-hole 108. The resonant transducer 100 measures stress (deformation) applied to the resonator 103 by detecting a change of resonant frequency of the resonator 103.

Figure 31:
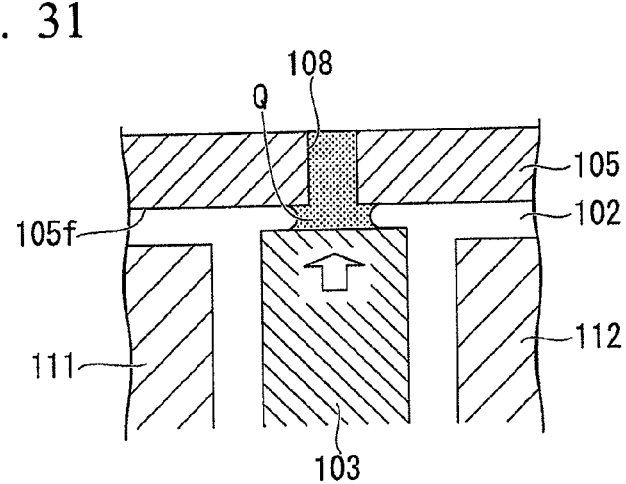
FIG. 31 is a drawing for describing a condition of discharging the etching liquid in the manufacturing method of the resonant transducer in the related art.

The resonant transducer 100 described above uses liquid in a process of discharging the etching waste liquid and a process of washing after the discharge process. As shown in FIG. 31, if a droplet Q of the liquid remains between the resonator 103 and the first polysilicon layer 105 including the through-hole 108, the resonator 103 is drawn to a side 105f of the first polysilicon layer 105 by meniscus force of the liquid. As the result, the resonator 103 adheres to the first polysilicon layer 105. Therefore, it remains possible that the resonant transducer 100 cannot detect the stress.

Also, in a process of forming plug with no space in the through-hole 108, the bigger a diameter of the through-hole 108 is, the thicker the second polysilicon layer 106 accumulated in the chamber 102 is. The second polysilicon layer 106 accumulated in an interspace between the resonator 103 and the first and second electrodes 111 and 112 lying at each side of the resonator 103 causes variation of magnitude of an output signal. Also, it remains possible that the first and second electrodes 111 and 112 are shorted by the second polysilicon layer 106 accumulated in the chamber 102, and the resonant transducer 100 cannot output the output signal.

Some embodiments of the present invention will be now described herein with reference to illustrative preferred embodiments. Those skilled in the art will recognize that many alternative preferred embodiments can be accomplished using the teaching of the present invention and that the present invention is not limited to the preferred embodiments illustrated herein for explanatory purposes.

A resonant transducer and a manufacturing method therefor according to embodiments of the present invention will be described below in detail, with references to the drawings. The present embodiment is described in detail in order to make the scope of the invention easier to understand, and the present embodiment does not limit the present invention inasmuch as there are no particular specifications. Some of the drawings used in the following description show enlarged views of significant portions for the sake of convenience in order to make the characteristics of the present invention easier to understand, and the dimensional ratios and other features of the constituent elements are not meant to be limited to those presented herein.

A Resonant Transducer

First Embodiment

Figure 1:
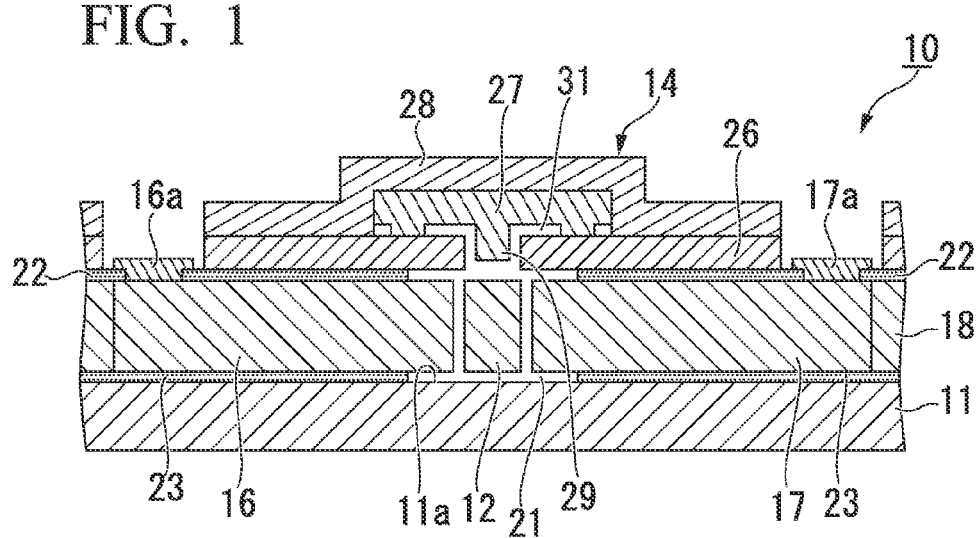
FIG. 1 is a sectional view illustrating the resonant transducer of a first embodiment.
Figure 2:
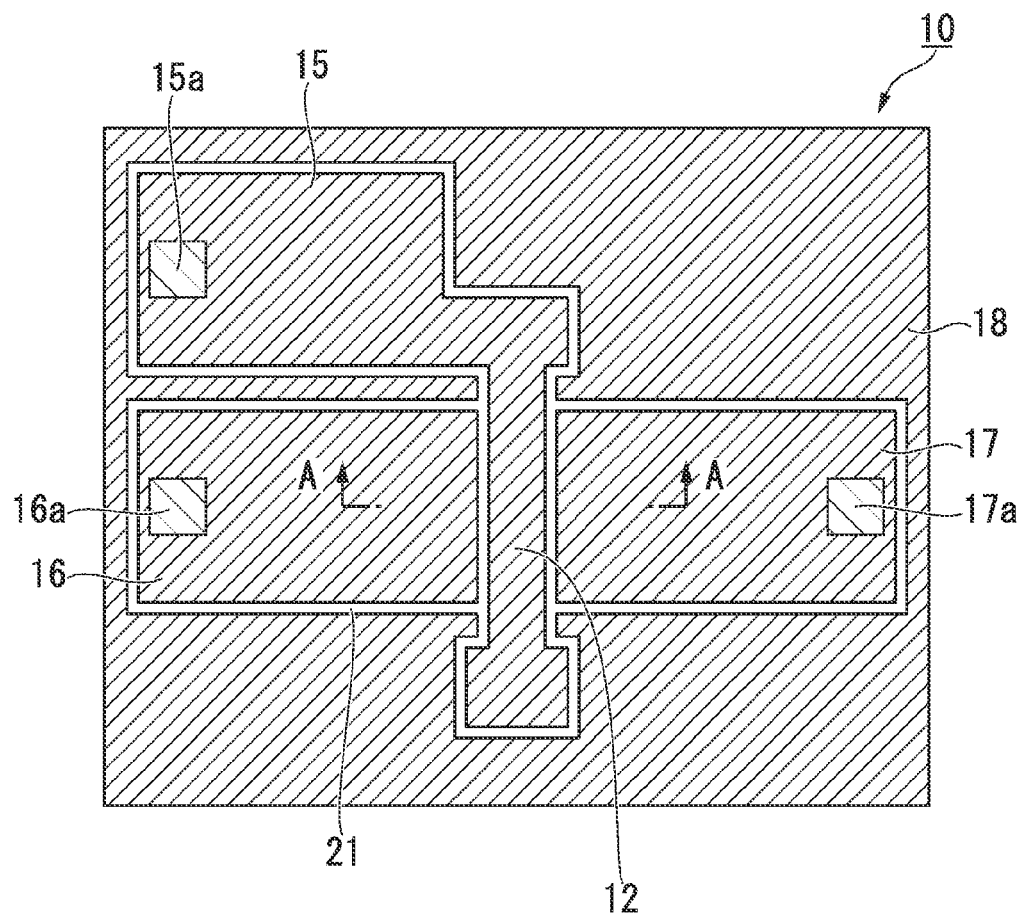
FIG. 2 is a plane view illustrating the resonant transducer of the first embodiment.

FIG. 1 is a sectional view illustrating the resonant transducer 10 of a first embodiment along a thickness direction. FIG. 2 is a plane view illustrating the resonant transducer 10 of the first embodiment without a shell. The resonant transducer 10 of an exemplary embodiment of the present invention includes a resonator 12 formed on a substrate 11 made of silicon single crystal. Interspaces are disposed around the resonator. Also, the resonant transducer 10 includes a shell 14 surrounding the resonator 12 and a chamber 21 with the substrate 11. The shell 14 is a multi-layer structure for the resonant transducer 10.

The chamber 21 is disposed on a side 11a of the substrate 11. The resonator 12, a first electrode 15, a second electrode 16, and a third electrode 17 are disposed in the chamber 21. Also, epitaxial layer 18 is disposed out of the chamber 21. The epitaxial layer 18, the resonator 12, the first electrode 15, the second electrode 16, and the third electrode 17 are made of same material such as a boron-doped low resistance P-type semiconductor.

The resonator 12 is integral with the first electrode 15 and electrically connected to the first electrode 15. When viewed from the shell 14, the resonator 12 is substantially narrow plate-like structure. A length of the resonator 12 in the thickness direction is longer than a width of the resonator 12 in a planar direction of the substrate 11. Also, predetermined tensile stress against the substrate 11 is added to the plate-like resonator 12. One end of the resonator 12 is integrally connected to the first electrode 15.

The second electrode 16 and the third electrode 17 are substantially rectangular-shaped electrodes. The second electrode 16 and the third electrode 17 are disposed in both sides of the resonator 12 in a longitudinal direction keeping predetermined gap from the resonator 12. Connection points 15a, 16a, and 17a to be connected to an external electrical circuit are respectively disposed on the first electrode 15, the second electrode 16, and the third electrode 17. For example, the connection points 15a, 16a, and 17a are made of metal.

Although insulated layer 22 is disposed between each of the electrodes 15 to 17 and the shell 14, the insulated layer 22 is not disposed in the chamber 21. Also, although insulated layer 23 is disposed between each of the electrodes 15 to 17 and the substrate 11, the insulated layer 23 is not disposed in the chamber 21. In a manufacturing process of the resonant transducer, the insulated layer 23 is formed by using a SOI substrate as the substrate 11. The manufacturing process of the resonant transducer will be described in detail.

Inside of the chamber 21 is kept in a predetermined degree of vacuum. For example, pressure in the chamber 21 is less than or equal to several tens of Pa so that measurement accuracy of the resonant frequency can be improved by suppressing energy loss of the resonator in a resonant state. The resonator 12, the first electrode 15, the second electrode 16, and the third electrode 17 are disposed leaving predetermined gap from members surrounding the chamber 21. The members surrounding the chamber 21 are the substrate 11, the epitaxial layer 18, and the shell 14.

Figure 3:
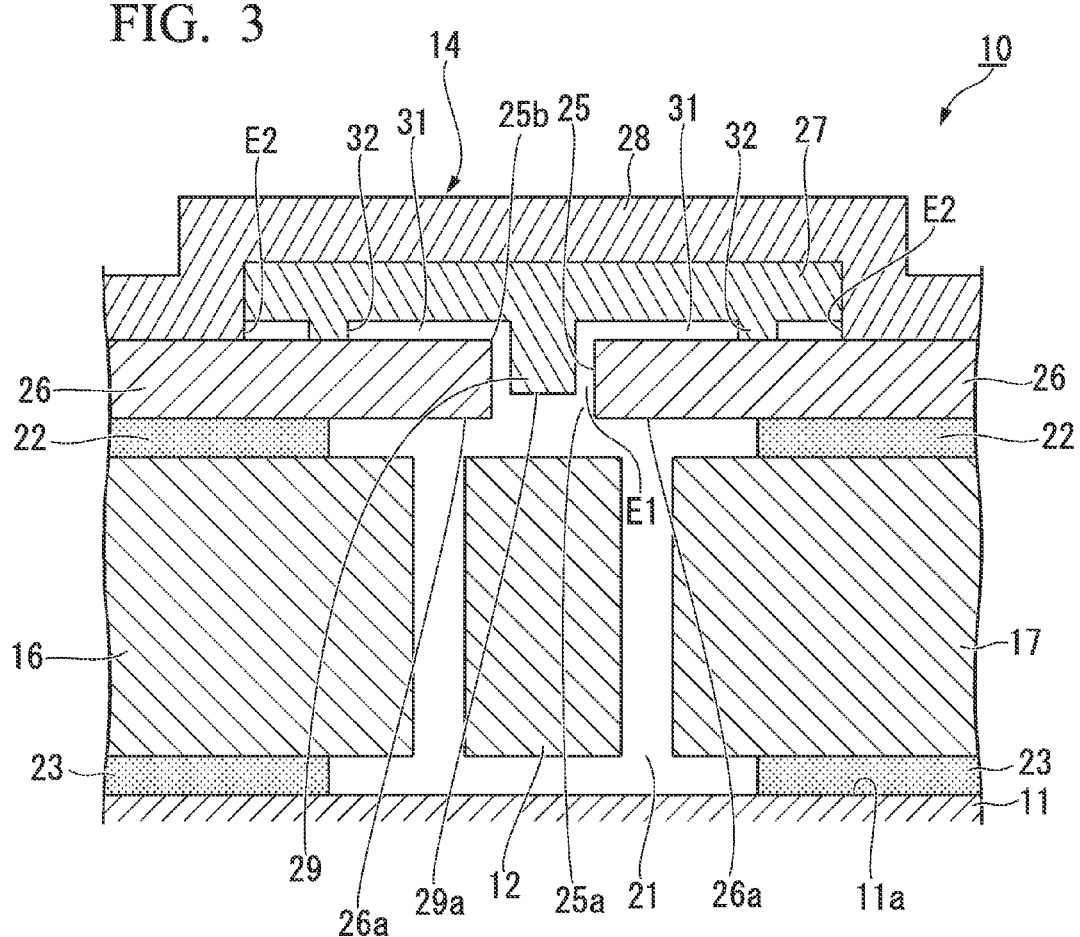
FIG. 3 is a zoomed sectional view around a main part of a resonator and a shell.

FIG. 3 is a zoomed sectional view around the resonator and the shell. The shell 14 includes a first polysilicon layer (first layer) 26, a second polysilicon layer (second layer) 27, and a third polysilicon layer (third layer) 28. The first polysilicon layer 26 is disposed over the insulated layer 22. The second polysilicon layer 27 is disposed over the first polysilicon layer 26. The third polysilicon layer 28 covers the first polysilicon layer 26 and the second polysilicon layer 27.

In the present embodiment, the three layers 26 to 28 (the first layer, the second layer, and the third layer) of the shell 14 may be made of polysilicon. However, the present embodiment is not limited to polysilicon. For example, the three layers 26 to 28 may be made of any one of amorphous silicon, SiC, SiGe, Ge, and so on.

The first polysilicon layer (first layer) 26 is in contact with the insulated layer 22. Also, the first polysilicon layer is disposed above the chamber. A through-hole 25 is disposed at an overlapped part of the first polysilicon layer 26 and the chamber 21. The through-hole 25 extends along a thickness direction of the first polysilicon layer 26. In following description, an opening portion of the through-hole 25 at a side of the chamber 21 may be called a first opening portion 25a. Also, an opening portion of the through-hole 25 at a side of the second polysilicon layer 27 may be called a second opening portion 25b.

Figure 4:
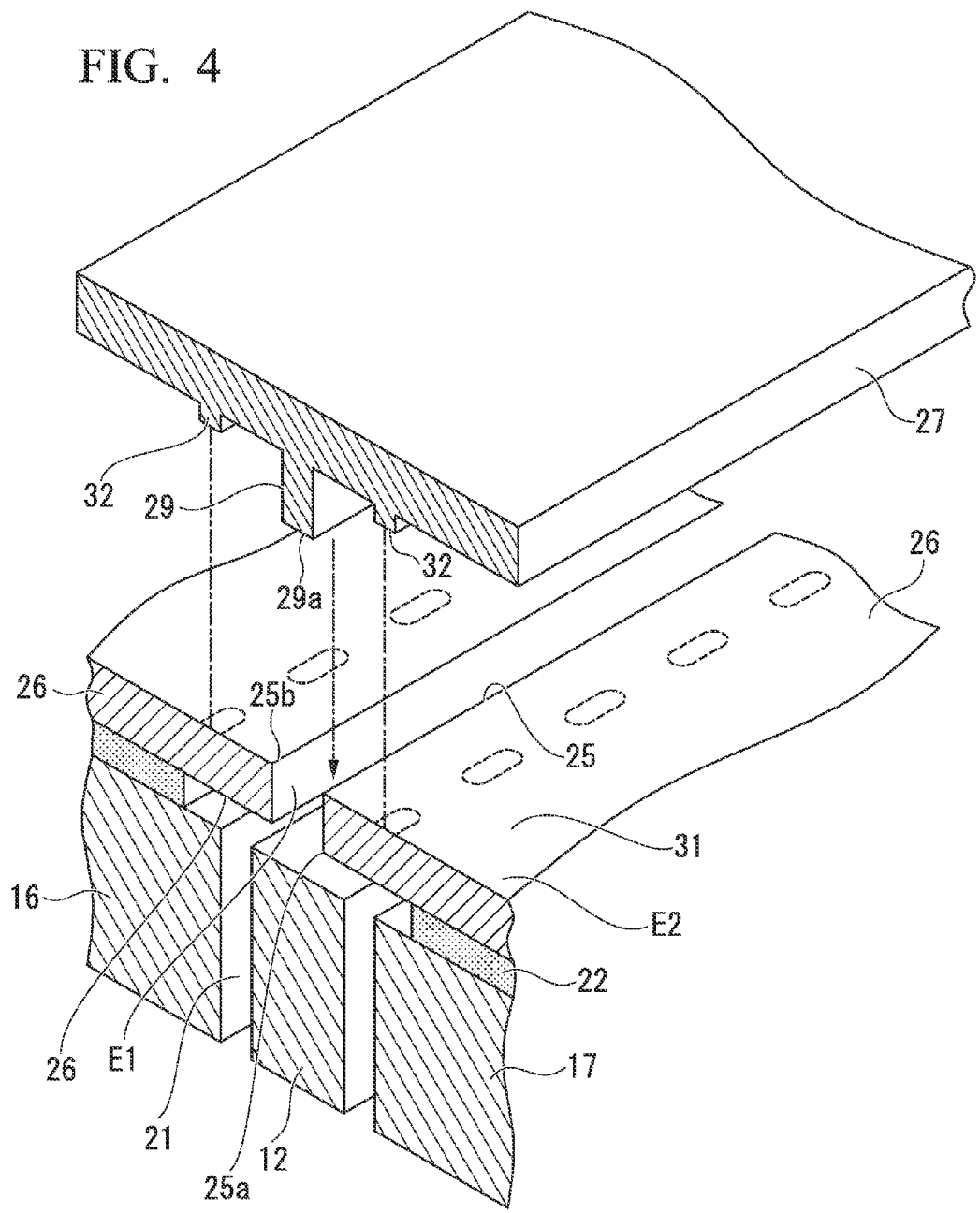
FIG. 4 is a zoomed diagrammatic perspective view illustrating a shape of a through-hole.

In the present embodiment, as shown in FIG. 4, when viewed from the third polysilicon layer 28, the first opening portion 25a and the second opening portion 25b of the through-hole 25 are rectangular-shaped sections extending along the resonator 12. More specifically, the through-hole 25 is a cuboid-shaped narrow space extending along a longitudinal direction of the resonator 12.

The second polysilicon layer 27 is disposed near the second opening portion 25b of the through-hole 25, and covers around the second opening portion 25b. Specifically, the second polysilicon layer 27 extends along a longitudinal direction of the through-hole 25 around the second opening portion 25b in predetermined width.

Also, the second polysilicon layer 27 has a projection. The projection 29 is integral with the second polysilicon layer 27 at a side of the through-hole 25 of the second polysilicon layer 27. The projection 29 enters from the second opening portion 25b into the through-hole 25. An end face 29a of the projection 29 is disposed in a position father away from the resonator 12 than a face 26a of the first polysilicon layer 26.

The third polysilicon layer 28 covers the first polysilicon layer 26 and the second polysilicon layer 27. Specifically, the third polysilicon layer 28 is in contact with the second polysilicon layer 27 in an area where the second polysilicon layer 27 exists. Also, the third polysilicon layer 28 is in contact with the first polysilicon layer 26 in outside of the second polysilicon layer 27.

In the shell 14 having the foregoing multi-layer structure, a gap 31 exists between the first polysilicon layer 26 and the second polysilicon layer 27. The gap 31 extends from a first gap E1 between the first polysilicon layer 26 and the projection 29 to a second gap E2 between the first polysilicon layer 26 and the second polysilicon layer 27. The first gap E1 is communicated with the second gap E2.

Specifically, in the sectional view shown in FIG. 1, the gap 31 is substantially L-shaped narrow space between the first polysilicon layer 26 and the second polysilicon layer 27. The first gap E1 is one open end of the gap 31. The first gap E1 exists between a side wall of the first opening portion 25a of the through-hole 25 and the projection 29 of the second polysilicon layer 27. Also, the second gap E2 is other open end of the gap 31. The second gap E2 is a gap between the first polysilicon layer 26 and the second polysilicon layer 27.

For example, the gap 31, that is to say, a distance between the first polysilicon layer 26 and the second polysilicon layer 27 may be a distance where etching liquid used in a process of forming the chamber 21 can flow in and flow out.

Non-empty spacers 32 are disposed on the second polysilicon layer 27. The spacers 32 are integral with the second polysilicon layer 27. The spacers 32 project from the second polysilicon layer 27. End faces of the spacers 32 come into contact with the first polysilicon layer 26. The spacers 32 form the second gap E2 to prevent the gap 31 from being narrowed by stress. A height of the spacer 32 is substantially equal to the gap 31.

As shown in FIG. 4, the spacers 32 are disposed along the longitudinal direction of the through-hole 25. Liquid flowing in the gap 31 (shown in the FIG. 3) such as the etching liquid flows between the spacers 32. For this reason, the spacers 32 form the second gap E2 of the gap 31, and prevent interrupting the flow of the liquid. In the present embodiment, each of the spacers 32 is long cylindroid-shaped.

Figure 5:
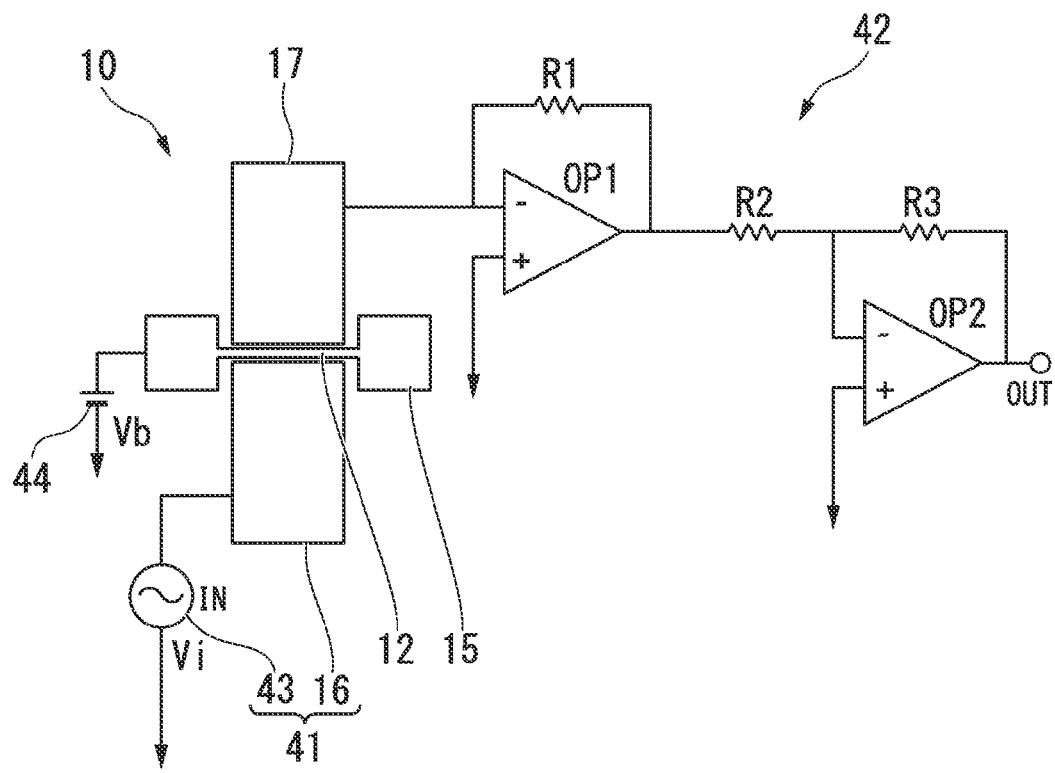
FIG. 5 is a circuit diagram illustrating the resonant transducer.

FIG. 5 is a circuit diagram of the resonant transducer. The resonant transducer 10 includes an exciting module 41 for exciting the resonator 12 and a vibration detecting module 42 for detecting vibration of the resonator 12. The exciting module 41 includes the second electrode 16 and a drive electrical source 43. The vibration detecting module 42 includes the first electrode 15, the third electrode 17, a bias electrical source 44, resistors R1, R2, and R3, operational amplifiers OP1 and OP2, and so on.

The drive electrical source 43 applies alternating-current voltage of predetermined drive voltage Vi. The bias electrical source 44 applies direct-current voltage of predetermined bias voltage Vb. The first electrode 15 is applied the constant bias voltage Vb from the bias electrical source 44. The second electrode 16 is applied the alternating drive voltage Vi from the drive electrical source 43. Detection signals according to vibrational frequency of the resonator 12 is output from the third electrode 17.

Operations of the resonant transducer are described below. After the constant bias voltage Vb is applied to the first electrode 15 and the alternating drive voltage Vi is applied to the second electrode 16, electrostatic suction power is generated between the resonator 12 connected to the first electrode 15 and the second electrode 16. At the time, the resonator 12 vibrates (resonates) at constant resonant frequency.

On the other hand, electrical charge is generated between the resonator 12 connected to the first electrode 15 and the third electrode 17 by the bias voltage Vb applied to the first electrode 15. When electrostatic capacity between the resonator 12 and the third electrode 17 is changed in accordance with vibration of the resonator 12, a detection signal according to the change of the electrostatic capacity is generated. The detection signal is alternating current. The operational amplifiers OP1 and OP2 amplify the detection signal. A counter reads the detection signal amplified by the operational amplifiers OP1 and OP2 as a voltage change so that the vibrational frequency of the resonator 12 can be measured.

When the resonator 12 is stressed by the stress, the vibrational frequency of the resonator 12 is changed in accordance with an amount of a strain of the resonator 12. An amount of the strain of the resonator 12, that is to say, the stress applied to the resonator 12 can be measured.

In the constitution, because it is possible to separate the second electrode 16 as an exciting electrode from the third electrode 17 as a detecting electrode, parasitic capacity between the second electrode 16 and the third electrode 17 decreases. As a result, cross talk of the drive voltage Vi on the detection circuit can be suppressed. Also, signal-to-noise ratio can be improved.

A Manufacturing Method of the Resonant Transducer

First Embodiment

A manufacturing method of the resonant transducer and an operation of the resonant transducer are described below.

FIG. 6 to FIG. 15 are zoomed sectional views of a main part of the resonant transducer for describing the manufacturing method of the resonant transducer in stages. Also, FIG. 6 to FIG. 15 are sectional views along a line A-A in FIG. 2.

Figure 6:
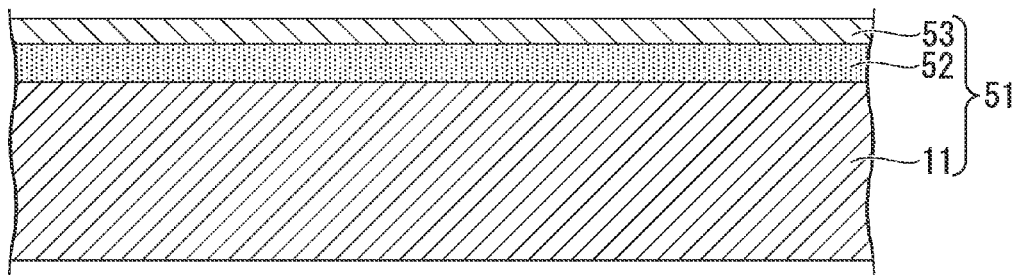
FIG. 6 is a sectional view illustrating the resonant transducer for describing a manufacturing method of the resonant transducer of the first embodiment.

First, as shown in FIG. 6, a SOI substrate 51 where an oxidized layer 52 and a superficial silicon layer 53 are formed on the substrate 11 is prepared. For example, a thickness of the oxidized layer 52 is about 2 micrometers. Also, a thickness of the superficial silicon layer 53 as an active layer is about 1 micrometer.

Figure 7:
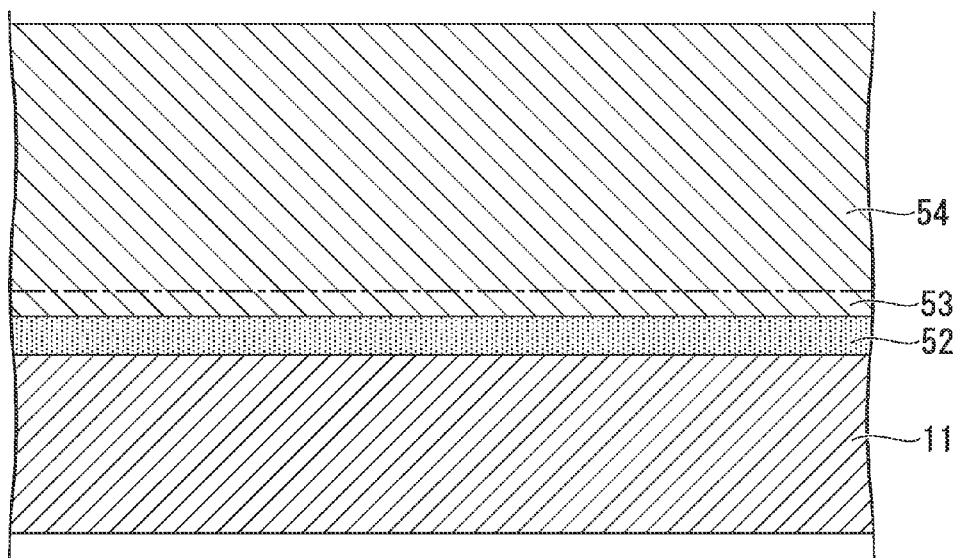
FIG. 7 is a sectional view of the resonant transducer for describing a manufacturing method of the resonant transducer of the first embodiment.

Next, as shown in FIG. 7, an epitaxial silicon layer 54 including a high level of boron is formed on the superficial silicon layer 53 as the active layer by epitaxial growth. The epitaxial silicon layer 54 including a high level of boron is low electrical resistance and behaves like a conductor. In post-process, the resonator 12, the first electrode 15, the second electrode 16, and the third electrode 17 (shown in FIG. 2) are formed in the epitaxial silicon layer 54.

Also, as the epitaxial silicon layer 54 including a high level of boron has grater tension stress than the substrate 11, the epitaxial silicon layer 54 generates tension to the resonator 12 formed in the post-process. When the stress is applied to the resonator 12 in a tension condition, the stress is proportional to a square of frequency, an extremely linear characteristic is obtained. On the other hand, as an operation in a compression stress condition has a non-linear characteristic, an operation of the resonant transducer 10 is performed in a tension stress condition.

A growth condition of the epitaxial silicon layer 54 including a high level of boron is (a) to (d) described below.
(a) growth temperature is 1030 degrees Celsius,
(b) in $H_2$ gas,
(c) dichlorosilane ($SiH_2Cl_2$) is used as ingredient gas of silicon, and
(d) diborane ($B_2H_6$) is used as ingredient gas of boron which is an impurity.

Also, the epitaxial silicon layer 54 including a high level of boron is grown to, for example, about 9 micrometers by performing the epitaxial growth for predetermined time. Then a sum of the thickness of the epitaxial silicon layer 54 and the thickness of the superficial silicon layer 53 is about 10 micrometers.

Figure 8:
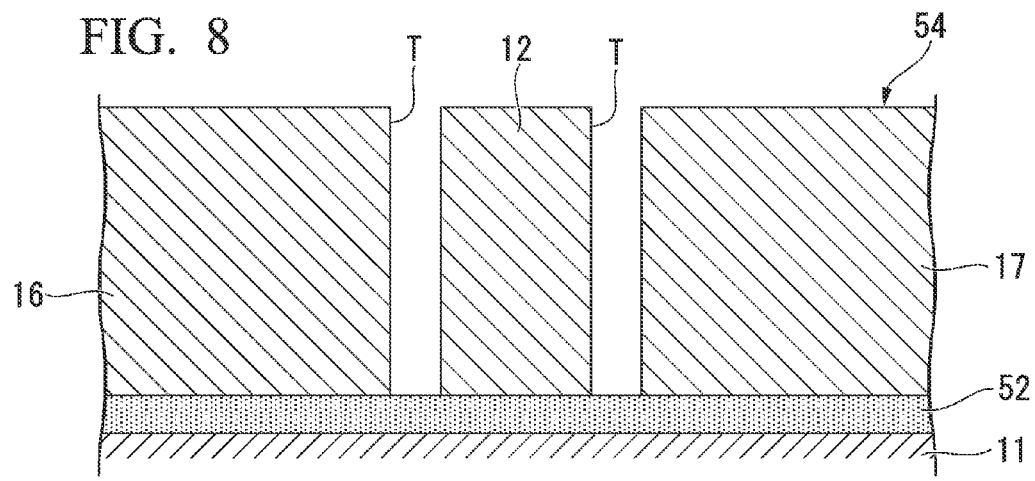
FIG. 8 is a sectional view of the resonant transducer for describing a manufacturing method of the resonant transducer of the first embodiment.

Next, as shown in FIG. 8, patterning of the epitaxial silicon layer 54 including a high level of boron is performed. Trenches T to become outline forms of the resonator 12, the first electrode 15 (shown in FIG. 2), the second electrode 16, and the third electrode 17 are formed on the epitaxial silicon layer 54. For example, the patterning of the epitaxial silicon layer 54 is performed by applying resist material. Also, the patterning is performed by a stepper apparatus.

For example, the stepper apparatus has resolution about 0.3 micrometers. Also, the stepper is capable of exposing submicron lines and spaces. The outline form pattern of the resonator 12, the first electrode 15, the second electrode 16, and the third electrode 17 are formed by the stepper apparatus.

The resist layer formed by the stepper apparatus is used as a mask, and the epitaxial silicon layer 54 is etched. The trenches T shaping the outline forms of the resonator 12, the first electrode 15, the second electrode 16, and the third electrode 17 are formed. For example, the epitaxial silicon layer 54 is etched by dry etching. The dry etching is performed until an etching position reaches the oxidized layer 52 on the substrate 11. The resonator 12, the first electrode 15, the second electrode 16, and the third electrode 17 are electrically separated each other.

In forming the trenches T by the dry etching, it is suitable that concave-convex portions are formed on a side wall of the trenches T by repeatedly performing a silicon etching process and a deposition process of a CF polymer. For example, stripes of which a width of the concave-convex portions is about 0.1 micrometer or more and a pitch of the concave-convex portions is about 0.1 to 1 micrometer are formed by adjusting an etching time and a deposition time.

Figure 9:
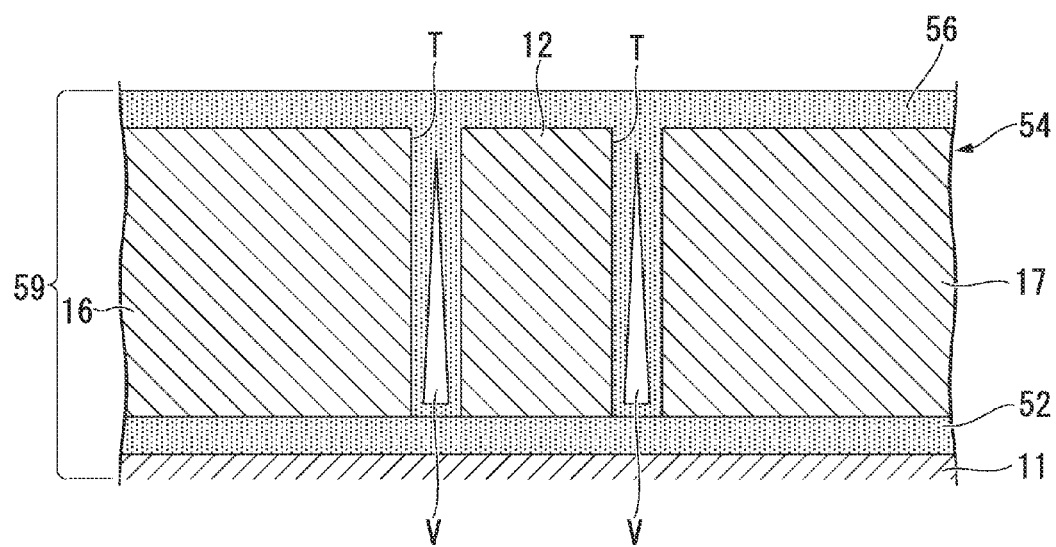
FIG. 9 is a sectional view of the resonant transducer for describing a manufacturing method of the resonant transducer of the first embodiment.

Next, as shown in FIG. 9, an insulated layer 56 is formed over the epitaxial silicon layer 54. Layered structure 59 includes the substrate 11, the epitaxial silicon layer 54, the oxidized layer 52, and the insulated layer 56. The trenches T shaping the outline forms of the resonator 12, the first electrode 15, the second electrode 16, and the third electrode 17 are filled with the insulated layer 56. The insulated layer 56 accumulates on the epitaxial silicon layer 54 by a predetermined thickness. For example, the insulated layer 56 is made of oxidized silicon. In forming the insulated layer 56, for example, open end portions of the trenches T are filled with a LP-CVD oxidized film or a plasma-CVD oxidized film of tetraethoxysilane (TEOS).

For example, the LP-CVD oxidized film is formed in a low pressure condition of 700 degrees Celsius and 50 Pascal by bubbling a TEOS tank, introducing nitrogen gas and oxygen gas, pyrolyzing the TEOS, and filling the trenches T with oxidized silicon.

The plasma CVD oxidized film is formed by a process of generating plasma by introducing TEOS and oxygen gas in vacuum, filling the trenches T with oxidized silicon on a substrate put on a stage heated to 400 degrees Celsius. As step coverage of the plasma CVD oxidized film is inferior in quality, the film is not easily formed in a deepest part of the trenches T and voids V are formed in a part of the insulated layer 56.

Figure 10:
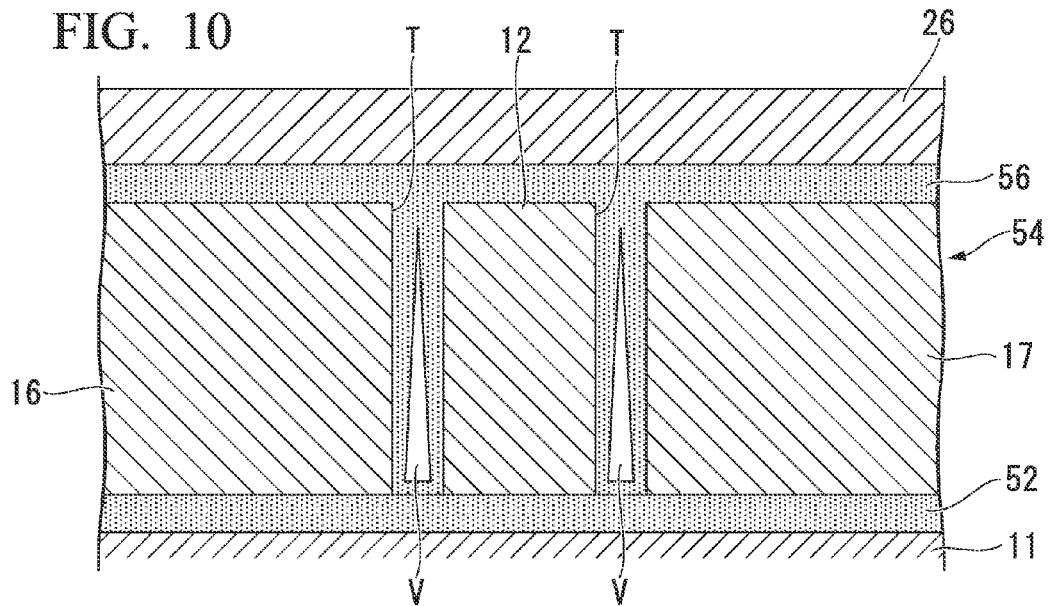
FIG. 10 is a sectional view of the resonant transducer for describing a manufacturing method of the resonant transducer of the first embodiment.

Next, as shown in FIG. 10, for example, the first polysilicon layer (first layer) 26 of which a thickness is several micrometers is formed over the insulated layer 56 covering the epitaxial silicon layer 54. The first polysilicon layer 26 is a part of the shell 14 covering the chamber 21 formed in the post-process.

Figure 11:
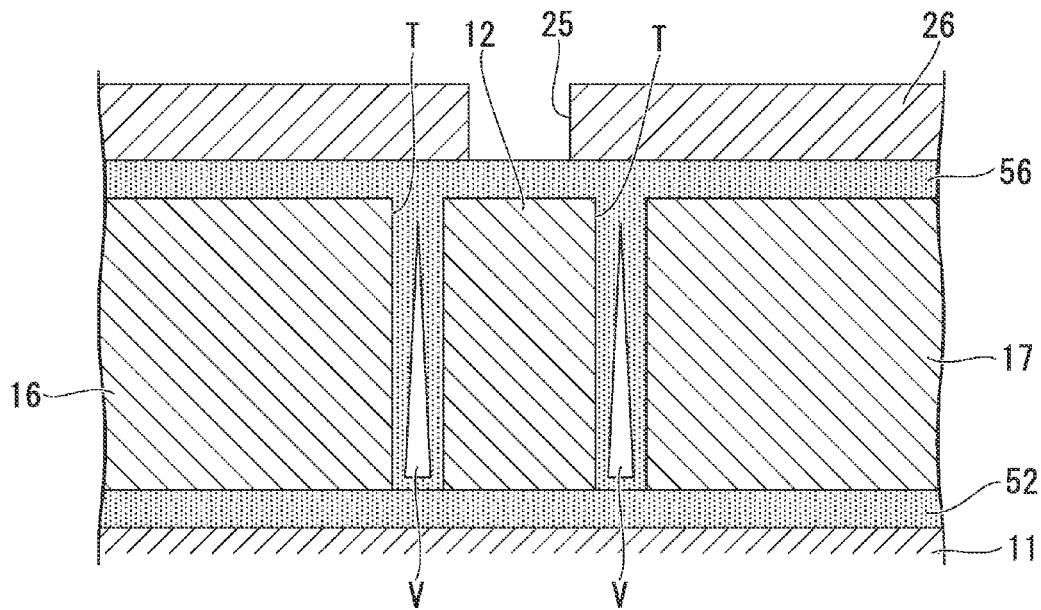
FIG. 11 is a sectional view of the resonant transducer for describing a manufacturing method of the resonant transducer of the first embodiment.

Next, as shown in FIG. 11, the through-hole 25 is formed in a part of the first polysilicon layer 26. For example, the through-hole 25 is formed in a position facing the resonator 12. Also, for example, after forming the resist layer for shaping an outline form of the first polysilicon layer 26, the through-hole 25 passing through the first polysilicon layer 26 in a thickness direction is formed by the dry etching. For example, the through-hole 25 is a cuboid-shaped narrow space extending along the longitudinal direction of the resonator 12 (shown in FIG. 4).

Figure 12:
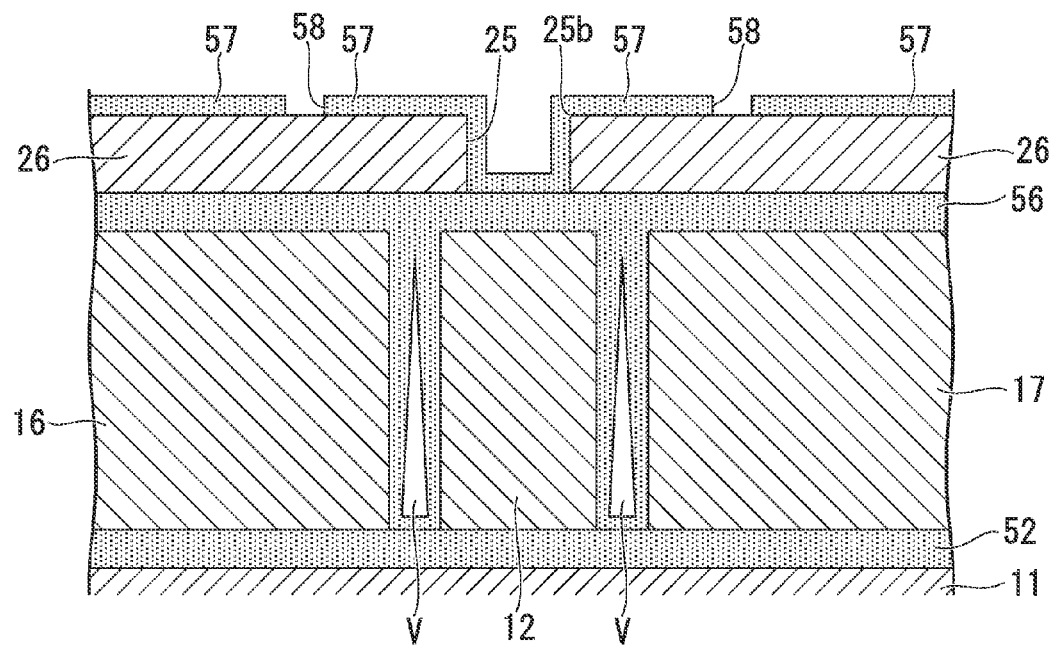
FIG. 12 is a sectional view of the resonant transducer for describing a manufacturing method of the resonant transducer of the first embodiment.

Next, as shown in FIG. 12, an oxide layer (sacrifice layer) 57 is formed. The oxide layer 57 covers the first polysilicon layer 26 and an inner surface of the through-hole 25. Dimples 58 for forming outer shapes of the spacers 32 of the second polysilicon layer 27 are formed around the second opening portion 25b of the through-hole 25. The spacers 32 will be formed in the post-process.

For example, a LP-CVD apparatus forms the oxide layer 57 of which thickness is about 100 nanometers and the dimples 58 are formed by using resist material removing only an area of the dimples 58 with buffered hydrofluoric acid.

Figure 13:
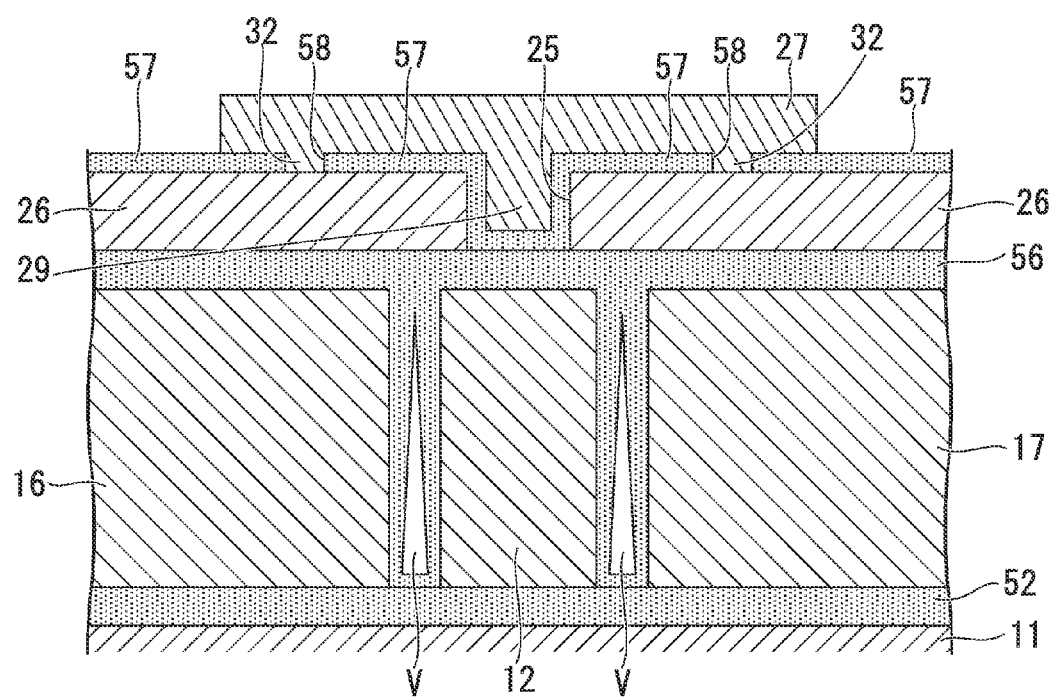
FIG. 13 is a sectional view of the resonant transducer for describing a manufacturing method of the resonant transducer of the first embodiment.

Next, as shown in FIG. 13, the second polysilicon layer (second layer) 27 is formed to cover the through-hole 25 and an area surrounding the through-hole 25. The projection 29 is integral with the second polysilicon layer 27. Also, the spacers 32 are integral with the second polysilicon layer 27. The projection 29 enters into the through-hole 25. The dimples 58 shape the spacers 32.

Figure 14:
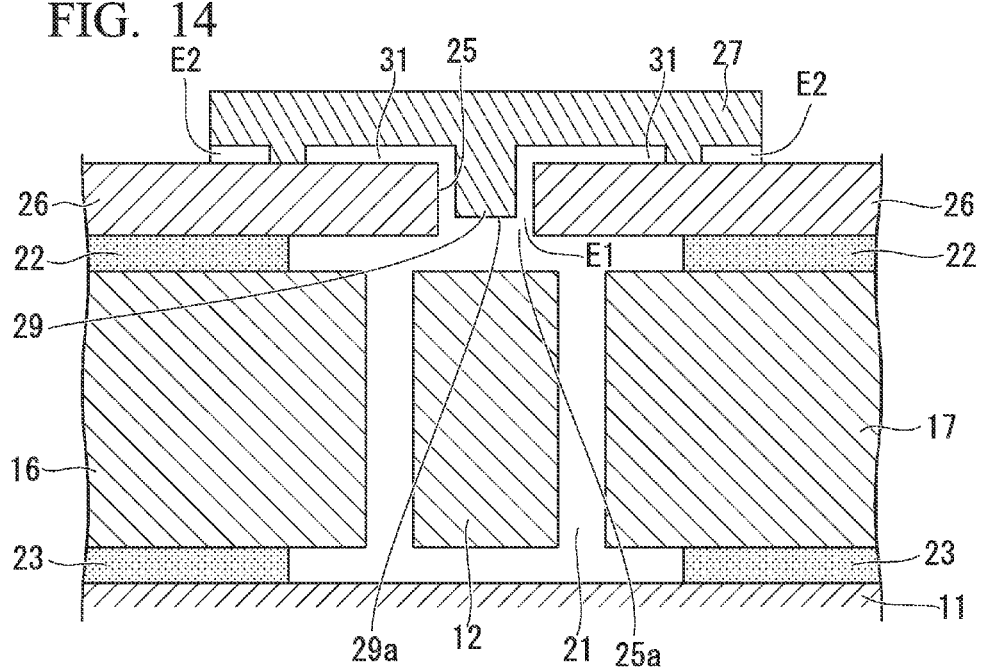
FIG. 14 is a sectional view of the resonant transducer for describing a manufacturing method of the resonant transducer of the first embodiment.

Next, as shown in FIG. 14, a whole of the oxide layer (sacrifice layer) 57 (shown in FIG. 13), the insulated layer 56 around the resonator 12 (shown in FIG. 13), and the oxidized layer 52 around the resonator 12 (shown in FIG. 13) are removed by etching with dilute HF solution. By the process, the chamber 21 is formed around the resonator 12, and the gap around the resonator 12 is kept.

On the other hand, by removing the oxide layer 57 formed between the first polysilicon layer 26 and the second polysilicon layer 27, the gap 31 is formed between the first polysilicon layer 26 and the second polysilicon layer 27. The gap 31 extends from a first gap E1 between the first polysilicon layer 26 and the projection 29 to a second gap E2 between the first polysilicon layer 26 and the second polysilicon layer 27. The first gap E1 is communicated with the second gap E2. The dilute HF solution reaches the insulated layer 56 around the resonator 12 and the oxidized layer 52 via the gap 31.

Waste solution of the dilute HF solution used for forming the chamber 21 by etching the insulated layer 56 and the oxidized layer 52 around the resonator 12 is discharged from inside to outside of the chamber 21 via the gap 31. When almost all of the waste solution is discharged and a little waste solution remains between the resonator 12 and the end face 29a of the projection 29 of the second polysilicon layer 27, meniscus force may be applied to the waste solution. If the meniscus force is applied to the waste solution, there is a worry that the resonator 12 bends toward the projection 29 of the second polysilicon layer 27 and the resonator 12 becomes deformed.

However, as the narrow gap 31 is formed between the first polysilicon layer 26 and the second polysilicon layer 27, a little waste solution around the first opening portion 25a is soaked up quickly by capillary action. By this process, around the first opening portion 25a of the through-hole 25, the projection 29 projects toward the chamber 21 so as to prevent the resonator 12 from being deformed and fixed. By decreasing a contact area of the end face 29a of the second polysilicon layer 27 and the resonator 12, in a process of removing the etching waste solution and water droplet of a washing process, it is preventable that the resonator 12 bends and adheres to an under surface of the first polysilicon layer 26. Also, the gap 31 between the first polysilicon layer 26 and the second polysilicon layer 27 prevents a variability of intensity of output signal, a variability of resonant frequency of the resonator 12, and output failure according to a short of electrodes.

Figure 15:
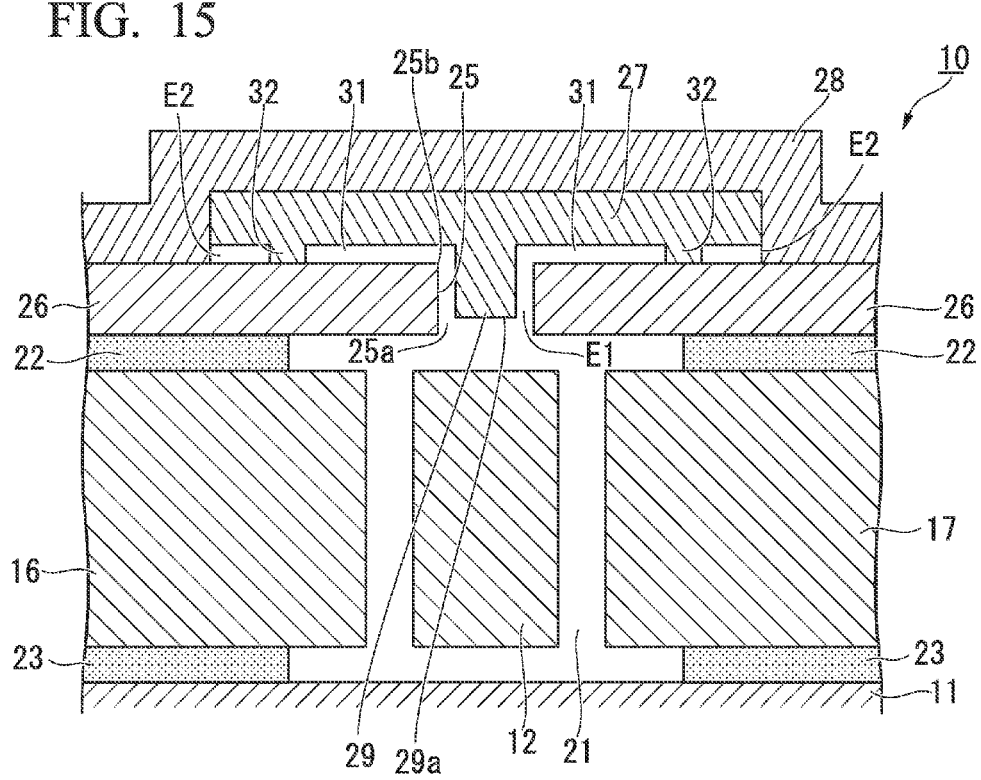
FIG. 15 is a sectional view of the resonant transducer for describing a manufacturing method of the resonant transducer of the first embodiment.

After that, as shown in FIG. 15, the third polysilicon layer (third layer) 28 is formed. The third layer 28 covers the first polysilicon layer 26 and the second polysilicon layer 27 for vacuum sealing. The third polysilicon layer 28 seals the gap 31 at a position of the second gap E2. The vacuum sealing by the third polysilicon layer 28 is performed in a condition that stretching strain is generated in the third polysilicon layer 28 or remaining compression strain is very little. For example, the vacuum sealing is performed by reduced pressure epitaxial apparatus at equal to or less than 900 degrees Celsius. $SiH_4$ or mixture of $SiH_4$ and hydrogen can be used as ingredient gas.

After that, holes exposing the connection points 15a, 16a, and 17a (shown in FIGS. 1 and 2) are formed at a position where the first polysilicon layer 26 is in contact with the third polysilicon layer 28. By these process, a sensor portion of the vibration transducer 10 can be formed.

As described above, in the resonant transducer, the manufacturing method therefor, and a multi-layer structure for a resonant transducer of the present embodiment, the contact area of the end face 29a and the resonator 12 is decreased. Also, it is preventable that the resonator 12 bends and adheres to the first polysilicon layer 26. Therefore, even if the meniscus force is applied to the droplet remaining between the resonator 12 and the first polysilicon layer 26, it is preventable that the resonator 12 adheres to the first polysilicon layer.

Also, as almost all the polysilicon layer in the chamber 21 can be restrained by the narrow gap 31 between the first polysilicon layer 26 and the second polysilicon layer 27, a variability of intensity of output signal, a variability of resonant frequency of the resonator 12, and output failure according to a short of electrodes are preventable.

Other embodiments of the resonant transducer will be described below. In each of the embodiments, same components as the first embodiment are numbered in the same manner as the first embodiment, and the explanation of the components are left out.

A Resonant Transducer

Second Embodiment

In the first embodiment, the through-hole 25 in the first polysilicon layer 26 is a cuboid-shaped narrow space extending along the longitudinal direction of the resonator 12. However, the shape of the through-hole 25 and the shape of the second polysilicon layer 27 covering the through-hole 25 are not limited thereto.

Figure 16:
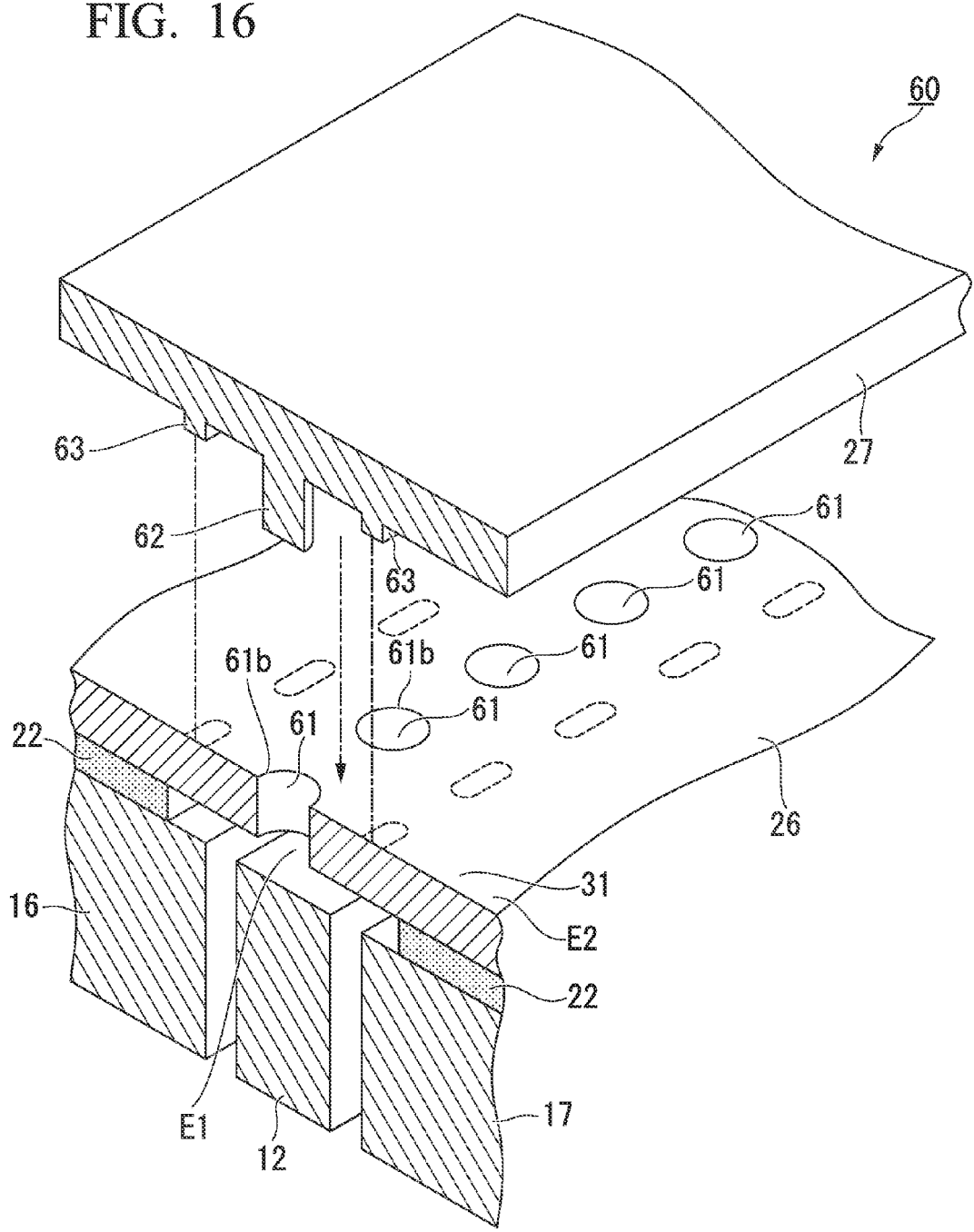
FIG. 16 is a zoomed diagrammatic perspective view illustrating a main part of the resonant transducer of the second embodiment.

In the resonant transducer 60 shown in FIG. 16, cylindrical-shaped through-holes 61 are disposed along the longitudinal direction of the resonator 12 on the first polysilicon layer (first layer) 26. When viewed from above, second opening portions 61b of the through-holes 61 are circular. The through-holes 61 are disposed along the longitudinal direction of the resonator 12. Projecting portions 62 are integral with the second polysilicon layer (second layer) 27. The projections 62 enter into the through-holes 61 respectively. A part of the gap 31 is cylindrical between an outer surface of the projection 62 and an inner surface of the through-hole 61.

Non-empty spacers 63 are integral with the second polysilicon layer 27. The spacers are in contact with a plane around second opening portions 61b of the through-holes 61 in the first polysilicon layer 26. For example, in the resonant transducer 60 shown in FIG. 16, the spacers 63 come into contact with the first polysilicon layer 26 at positions surrounding the second opening portions 61b of the through-holes 61.

A Resonant Transducer

Third Embodiment

Figure 17:
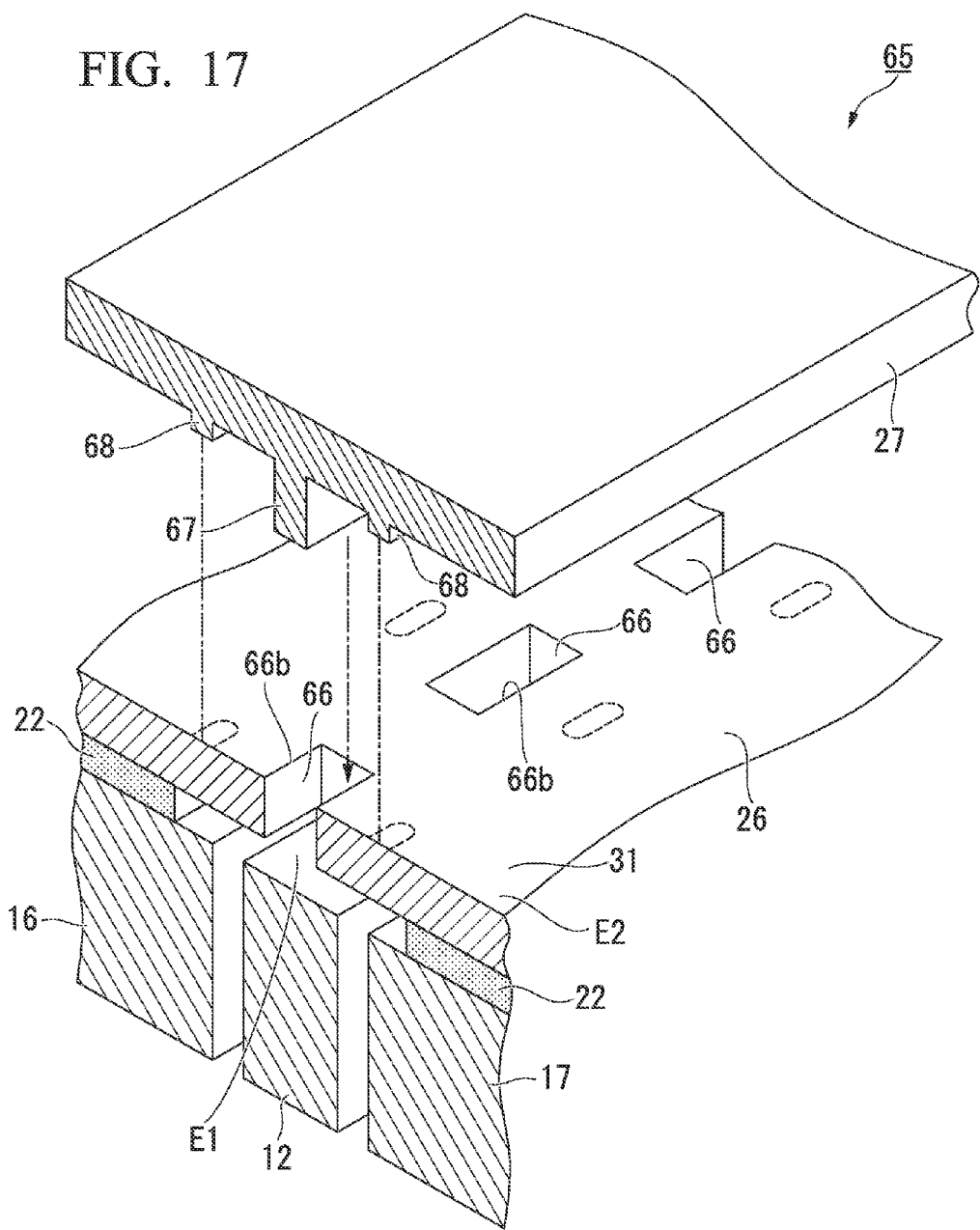
FIG. 17 is a zoomed diagrammatic perspective view illustrating a main part of the resonant transducer of the third embodiment.

In the resonant transducer 65 shown in FIG. 17, cuboid-shaped through-holes 66 are disposed along the longitudinal direction of the resonator 12 on the first polysilicon layer (first layer) 26. When viewed from above, second opening portions 66b of the through-holes 66 are rectangular. The through-holes 66 are disposed along the longitudinal direction of the resonator 12. Projecting portions 67 are integral with the second polysilicon layer (second layer) 27. The projections 67 enter into the through-holes 66 respectively. A part of the gap 31 is rectangular-section cylindrical between an outer surface of the projection 67 and an inner surface of the through-hole 66.

Non-empty spacers 68 are integral with the second polysilicon layer 27. The spacers 68 touch the first polysilicon layer 26 around second opening portions 66b of the through-holes 66. For example, in the resonant transducer 65 shown in FIG. 17, the spacers 68 come into contact with the first polysilicon layer 26 at both sides along a longitudinal direction of the second opening portions 66b of the through-holes 66.

The shapes of the through-holes 66 may be oval-shapes, ellipse-shapes, triangular-shapes, polygonal-shapes, indefinite-shapes, or the like. The shapes of the through-holes 66 are not limited thereto.

The shapes of the spacers forming the gap 31 (shown in FIG. 3) between the first polysilicon layer 26 and the second polysilicon layer 27 are not limited to the shapes shown in the first embodiment or the second embodiment. For example, the spacers may be irregular concavities and convexities formed on at least one of the first polysilicon layer 26 and the second polysilicon layer 27 to allow passage of fluid. In this case, the spacers may be rough surfaces on at least one of the first polysilicon layer 26 and the second polysilicon layer 27.

A Resonant Transducer

Fourth Embodiment

Figure 18:
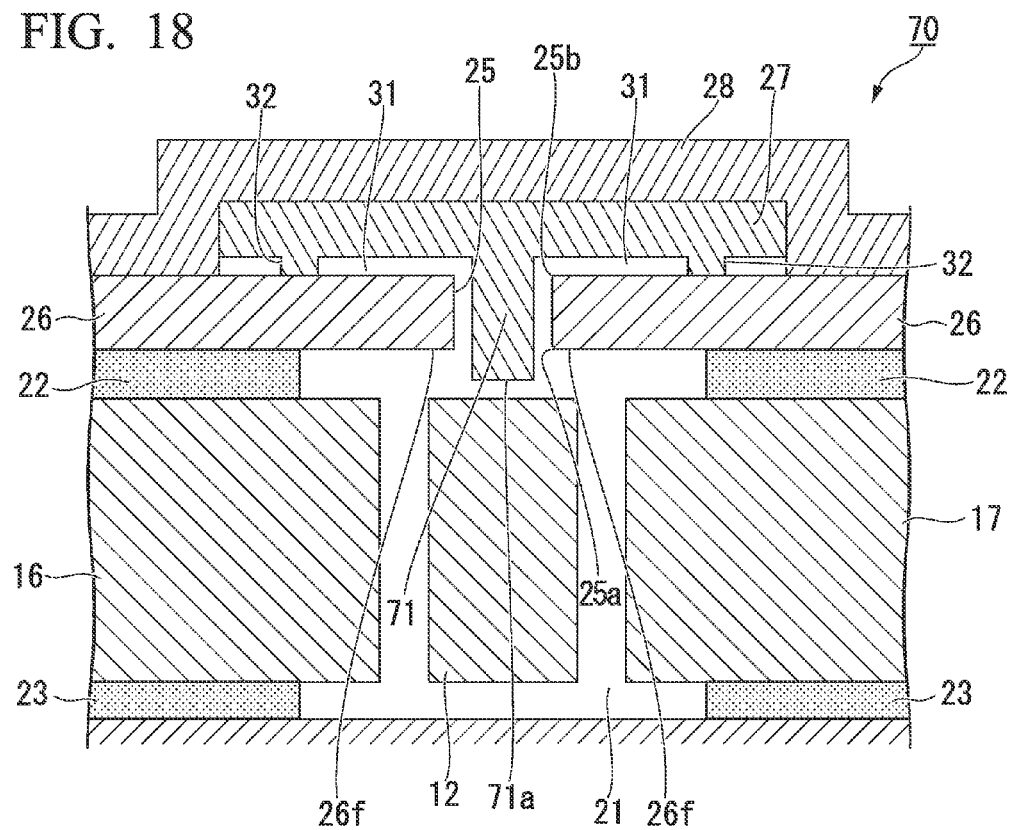
FIG. 18 is a zoomed diagrammatic perspective view illustrating a main part of the resonant transducer of the fourth embodiment.

FIG. 18 is a zoomed sectional view illustrating a resonant transducer of the fourth embodiment. In the transducer 70 of the present embodiment, the first polysilicon layer (first layer) 26 of the shell 14 has the through-hole 25 extending toward the chamber 21. The resonator 12 is disposed in the chamber 21 and vibrates. A projection 71 is integral with the second polysilicon layer (second layer) 27. The projection 71 enters into the through-hole 25. The gap 31 exists between the outer surface of the projection 71 and the inner surface of the through-holes 25.

An end face 71a of the projection 71 is disposed immediately above the resonator 12. A distance between the end face 71a and the resonator 12 is shorter than a distance between a face 26f of the first polysilicon layer 26 and the resonator 12. Therefore, the projection 71 extends from the second polysilicon layer 27 to the first opening portion 25a, and projects into the chamber 21.

As the projection 71 projects into the chamber 21, it is possible to prevent the resonator 12 from coming into contact with the first polysilicon layer 26 more surely. For example, in a process of forming the chamber 21 of the resonant transducer 70, when discharging the etching waste liquid through the gap 31, the meniscus force may be applied to the waste liquid remaining between the resonator 12 and the first opening portion 25a of the first polysilicon layer 26. Even if the resonator 12 bends widely toward the first polysilicon layer 26 by the meniscus force, the resonator 12 comes into contact with the end face 71a of the projection 71 projecting into the chamber 21.

Therefore, it is preventable that the resonator 12 bends widely and comes into contact with the face 26f of the first polysilicon layer 26. Specifically, as the end face 71a of the projection 71 is narrower than the resonator 12, even if the resonator 12 bends and comes into contact with the end face 71a of the projection 71, a contact area of the resonator 12 and the end face 71a is small. Therefore, it is preventable that the resonator 12 adheres to the end face 71a.

A Manufacturing Method of the Resonant Transducer

Second Embodiment

Figure 19:
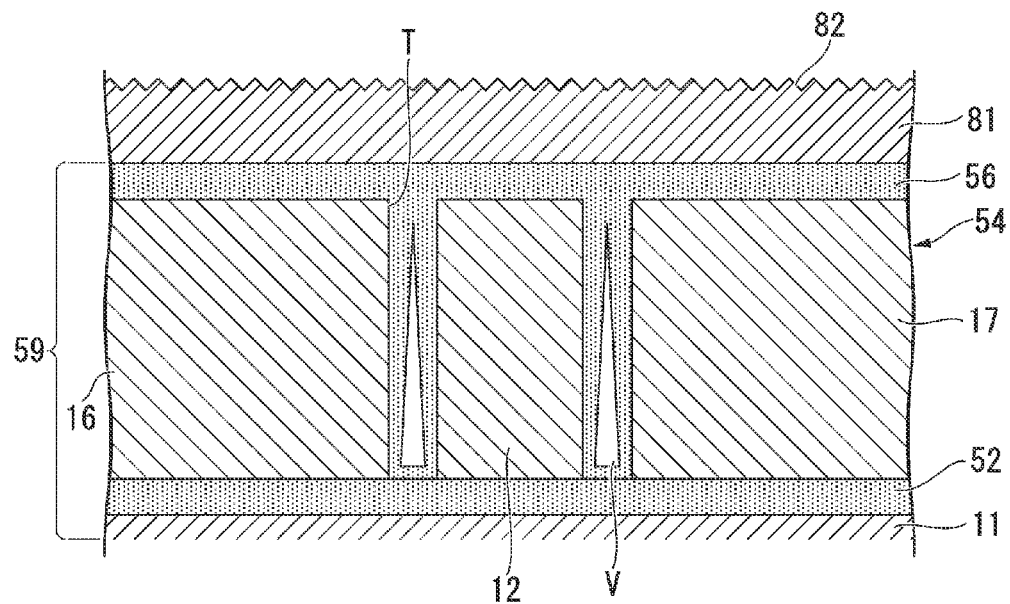
FIG. 19 is a sectional view illustrating the resonant transducer for describing a manufacturing method of the resonant transducer of the second embodiment.

FIG. 19 to FIG. 23 are zoomed sectional views of a main part of the resonant transducer for describing the manufacturing method of the resonant transducer in stages in a second embodiment. FIG. 19 is a drawing for describing a process corresponding to the FIG. 10 in the manufacturing method of the resonant transducer of the first embodiment. As shown in FIG. 19, for example, a first polysilicon layer (first layer) 81 of which a thickness is several micrometers is formed on the insulated layer 56. The layered structure 59 includes the substrate 11, the epitaxial silicon layer 54, the oxidized layer 52, and the insulated layer 56. For example, the first polysilicon layer 81 is formed by an epitaxial apparatus. Microscopic concavities and convexities 82 according to a grain size are formed on an upper surface of the first polysilicon layer 81.

Figure 20:
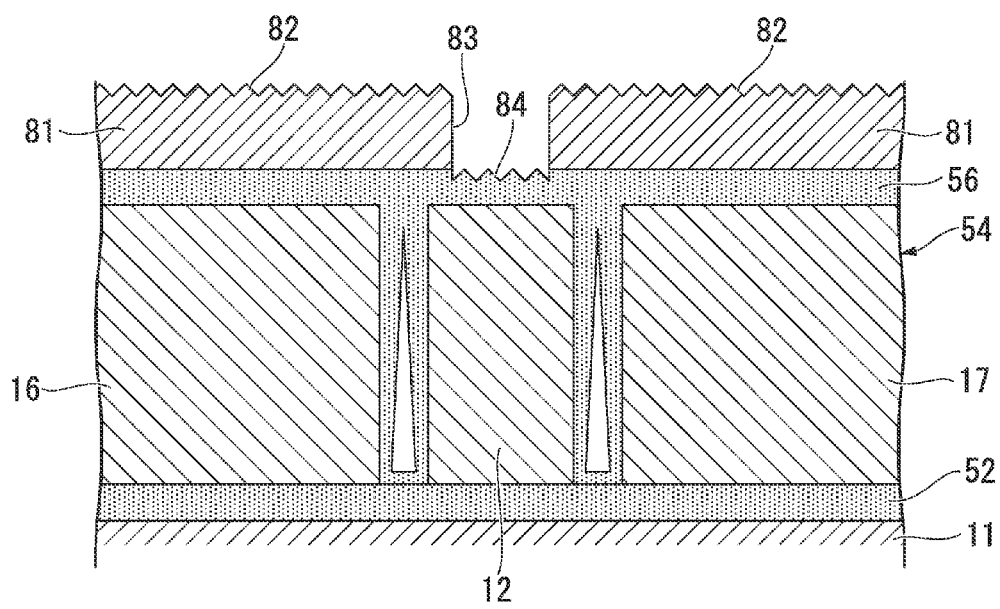
FIG. 20 is a sectional view illustrating the resonant transducer for describing a manufacturing method of the resonant transducer of the second embodiment.

Next, as shown in FIG. 20, the through-hole 83 is formed in a part of the first polysilicon layer 81. For example, the through-hole 83 is formed immediately above the resonator 12. Also, for example, after forming the resist layer for shaping an outline form of the first polysilicon layer 81, the through-hole 83 is formed by the dry etching. The through-hole 83 passes through the first polysilicon layer 81 in a thickness direction. At this time, microscopic concavities and convexities 84 are formed on a bottom face of the through-hole 83.

The process shown in FIG. 19 and the process shown in FIG. 20 can be performed, for example, as a sequence of etching processes of dry etching in which an etching ratio of a polysilicon and an insulation layer (oxide silicon) is low.

Figure 21:
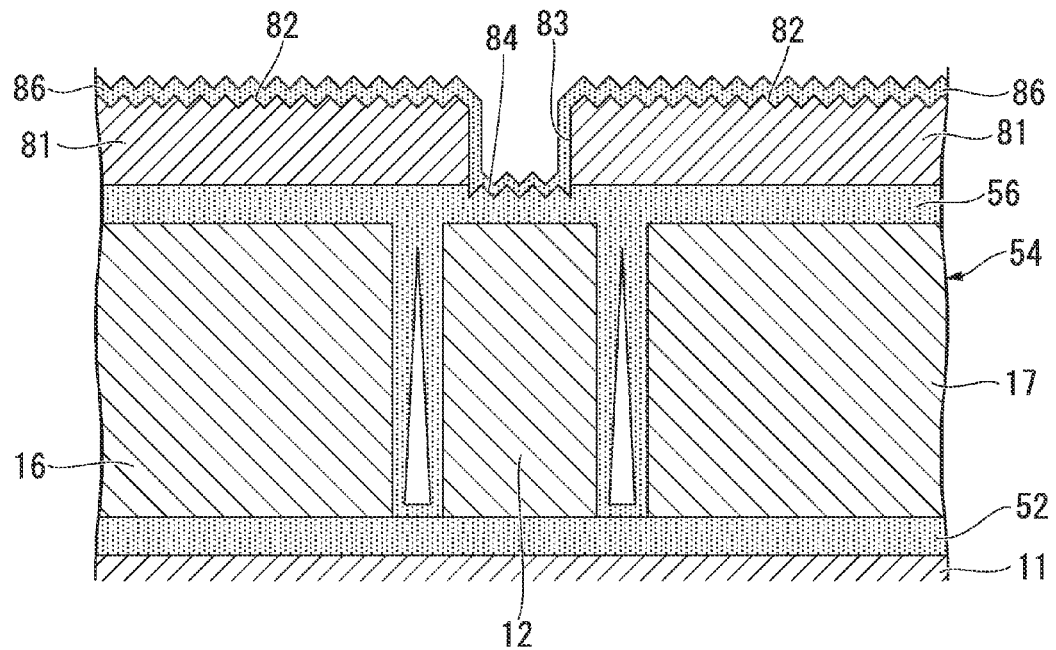
FIG. 21 is a sectional view illustrating the resonant transducer for describing a manufacturing method of the resonant transducer of the second embodiment.

Next, as shown in FIG. 21, an oxide layer 86 is formed. The oxide layer 86 covers the microscopic concavities and convexities 82 formed on the first polysilicon layer 81, an inner surface of the through-hole 83, and the microscopic concavities and convexities 84 formed on the bottom face of the through-hole 83.

Figure 22:
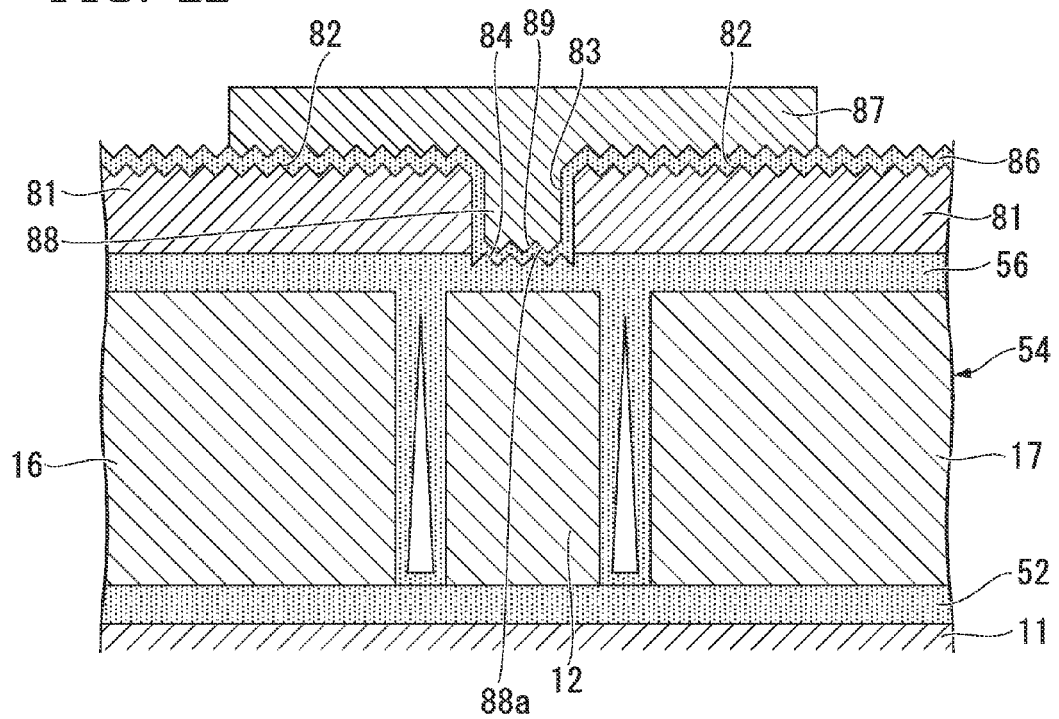
FIG. 22 is a sectional view illustrating the resonant transducer for describing a manufacturing method of the resonant transducer of the second embodiment.

Next, as shown in FIG. 22, the second polysilicon layer (second layer) 87 is formed to cover the through-hole 83 and an area surrounding the through-hole 83. A projection 88 is formed on the bottom surface of the second polysilicon layer 87. The projection 88 enters into the through-hole 83 covered with the oxide layer 86, and extends to the insulated layer 56. Concavities and convexities 89 are formed on the microscopic concavities and convexities 84. Specifically, the concavities and convexities 89 are formed on an end face 88a of the projection 88.

Figure 23:
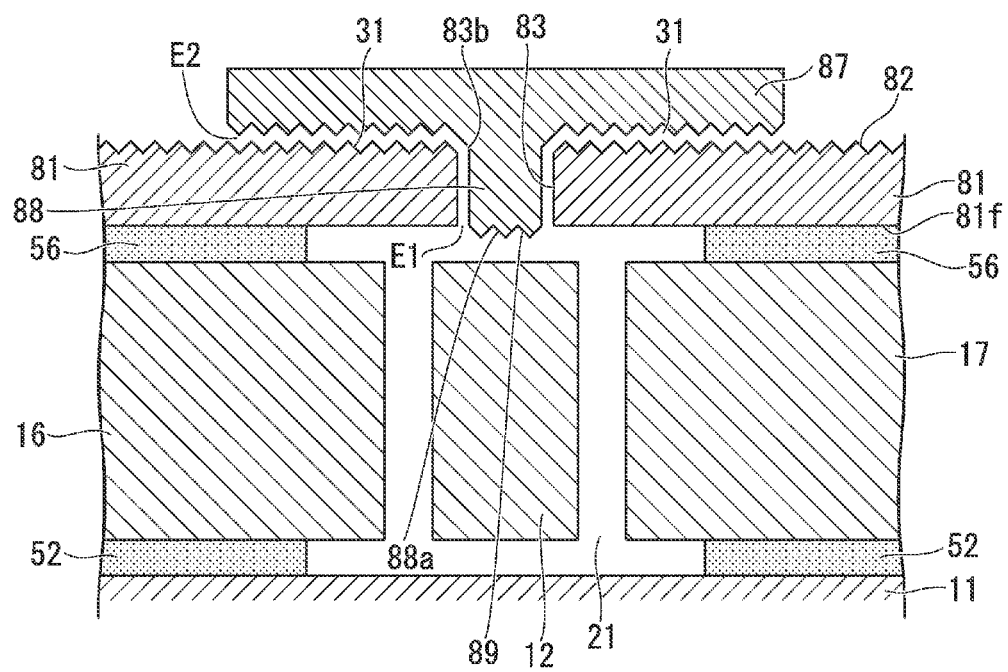
FIG. 23 is a sectional view illustrating the resonant transducer for describing a manufacturing method of the resonant transducer of the second embodiment.

Next, as shown in FIG. 23, a whole of the oxide layer 86, the insulated layer 56 around the resonator 12, and the oxidized layer 52 around the resonator 12 are removed by etching with dilute HF solution. By the process, the chamber 21 is formed around the resonator 12. The gap around the resonator 12 is kept.

On the other hand, by removing the oxide layer 86 formed between the first polysilicon layer 81 and the second polysilicon layer 87, the gap 31 is formed between the first polysilicon layer 81 and the second polysilicon layer 87. The gap 31 extends from a first gap E1 between the first polysilicon layer 81 and the projection 88 to a second gap E2 between the first polysilicon layer 81 and the second polysilicon layer 87. The first gap E1 is communicated with the second gap E2. The dilute HF solution flows into the chamber 21 and flows from the chamber 21 via the gap 31.

By the manufacturing method of the resonant transducer in the present embodiment, even if a little waste solution remains between the resonator 12 and the first polysilicon layer 81 and the meniscus force of the waste solution bends the resonator 12 widely toward the first polysilicon layer 81, the resonator 12 comes into contact with the end face 88a of the projection 88 projecting into the chamber 21. Therefore, it is preventable that the resonator 12 adheres to the first polysilicon layer 81.

Further, in the manufacturing method of the second embodiment, as the microscopic concavities and convexities 89 are formed on the end face 88a of the projection 88, a contact area of the projection 88 and the resonator 12 is very small. Therefore, as the resonator 12 does not adhere to the end face 88a of the projection 88, it is preventable that the resonator 12 becomes deformed.

A Manufacturing Method of the Resonant Transducer

Third Embodiment

Figure 24:
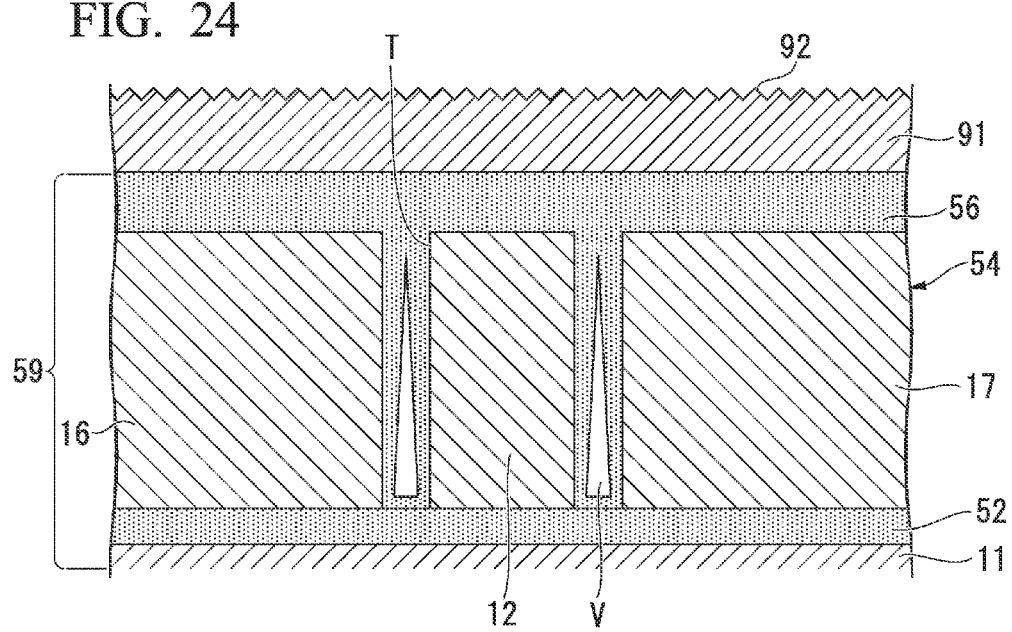
FIG. 24 is a sectional view illustrating the resonant transducer for describing a manufacturing method of the resonant transducer of the third embodiment.

FIG. 24 to FIG. 29 are zoomed sectional views of a main part of the resonant transducer for describing the manufacturing method of the resonant transducer in stages in a third embodiment. FIG. 24 is a drawing for describing a process corresponding to the FIG. 10 in the manufacturing method of the resonant transducer of the first embodiment. As shown in FIG. 24, for example, a first polysilicon layer (first layer) 91 of which a thickness is several micrometers is formed on the insulated layer 56. The layered structure 59 includes the substrate 11, the epitaxial silicon layer 54, the oxidized layer 52, and the insulated layer 56. Then, microscopic concavities and convexities 92 are formed on an upper surface of the first polysilicon layer 91 by the dry etching.

Figure 25:
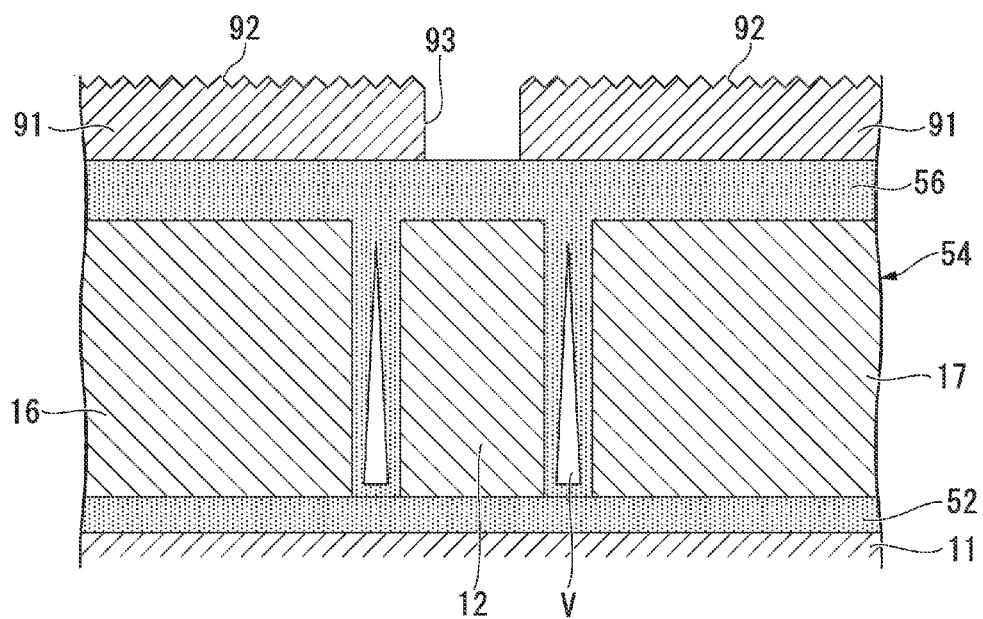
FIG. 25 is a sectional view illustrating the resonant transducer for describing a manufacturing method of the resonant transducer of the third embodiment.

Next, as shown in FIG. 25, the through-hole 93 passing through the first polysilicon layer 91 is formed. For example, the through-hole 93 is formed immediately above the resonator 12. Also, for example, after forming the resist layer for shaping an outline form of an opening portion of the through-hole 93 on the first polysilicon layer 91, the through-hole 93 is formed by the dry etching. The through-hole 93 passes through the first polysilicon layer 91 in a thickness direction.

Figure 26:
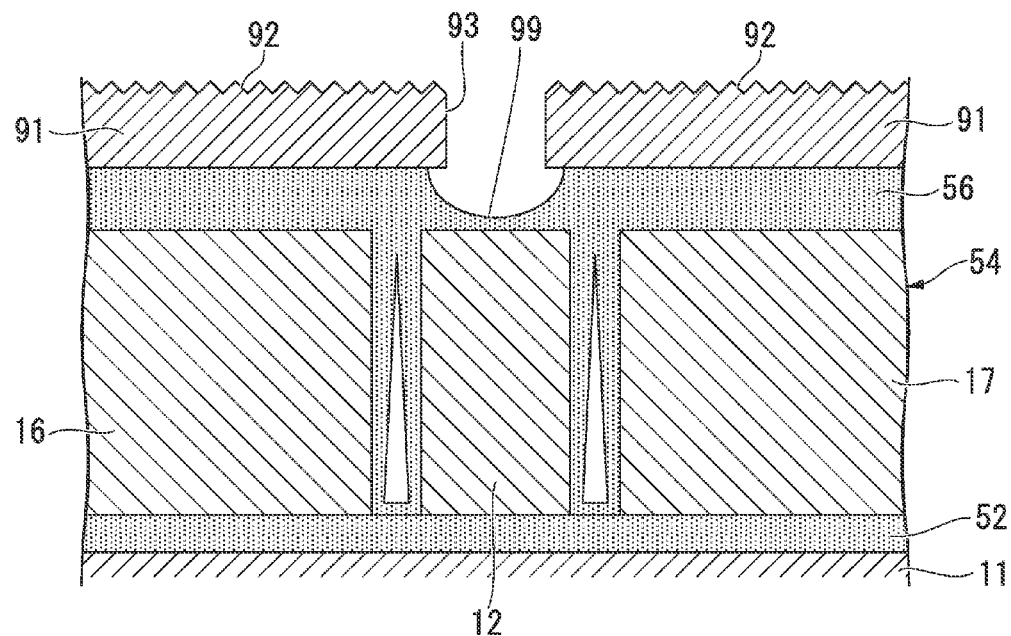
FIG. 26 is a sectional view illustrating the resonant transducer for describing a manufacturing method of the resonant transducer of the third embodiment.

Further, as shown in FIG. 26, by isotropically etching the insulated layer 56 from the through-hole 93, a bottom face 99 is formed in the insulated layer 56. A diameter of the bottom face 99 is longer than a width of the through-hole 93. A cross-section shape of the bottom face 99 is semicircle. For example, as the characteristic of the etching liquid used for the etching, an etching rate of oxide silicon is higher than an etching rate of polysilicon. The etching liquid can be used for isotropically etching.

Figure 27:
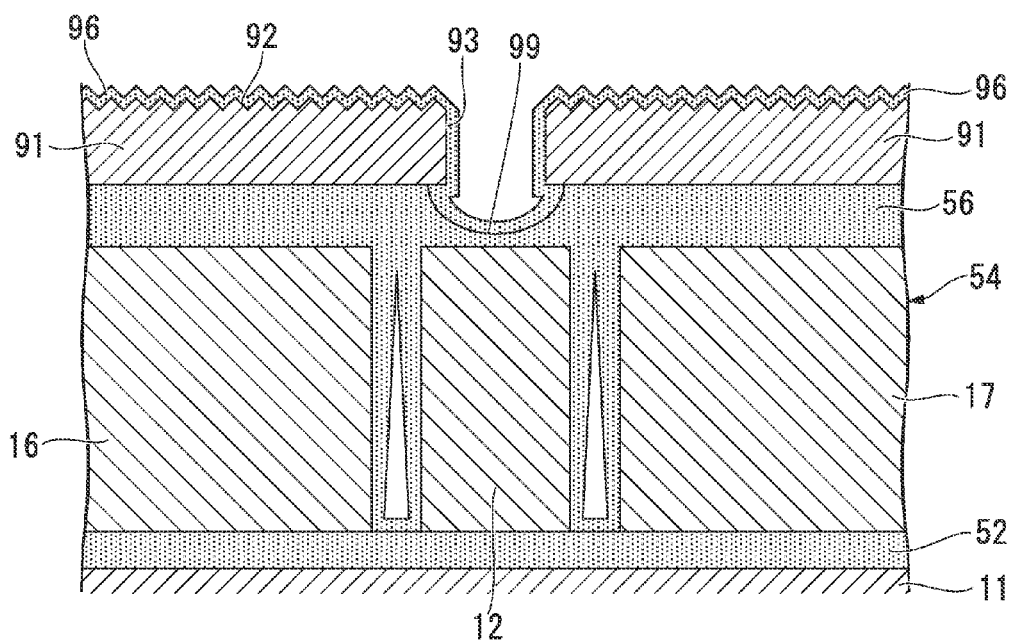
FIG. 27 is a sectional view illustrating the resonant transducer for describing a manufacturing method of the resonant transducer of the third embodiment.

Next, as shown in FIG. 27, an oxide layer 96 is formed. The oxide layer 96 covers the microscopic concavities and convexities 92 formed on the first polysilicon layer 91, an inner surface of the through-hole 93, and the bottom face 99 of the insulated layer 56.

Figure 28:
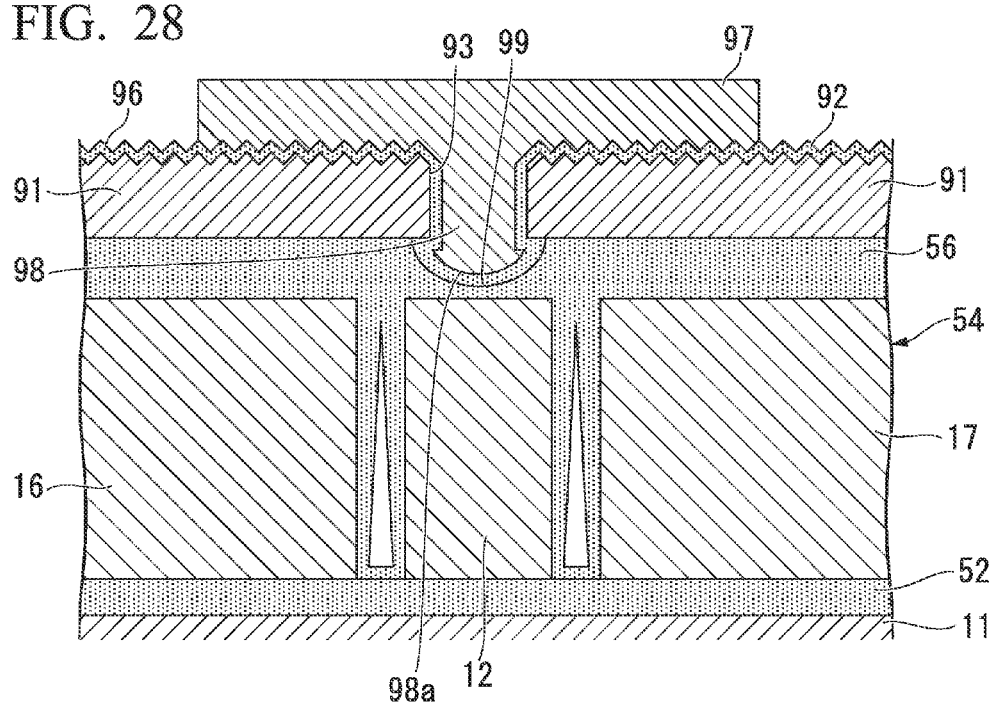
FIG. 28 is a sectional view illustrating the resonant transducer for describing a manufacturing method of the resonant transducer of the third embodiment.

Next, as shown in FIG. 28, the second polysilicon layer 97 is formed. The second polysilicon layer 97 covers the through-hole 93 and an area surrounding the through-hole 93. A projection 98 is formed on the bottom surface of the second polysilicon layer 97. The projection 98 enters into the through-hole 93 covered with the oxide layer 96. The projection 98 has an end face 98a of which shape depends on a shape of the bottom face 99. A cross-section shape of the bottom face 99 is semicircle.

Figure 29:
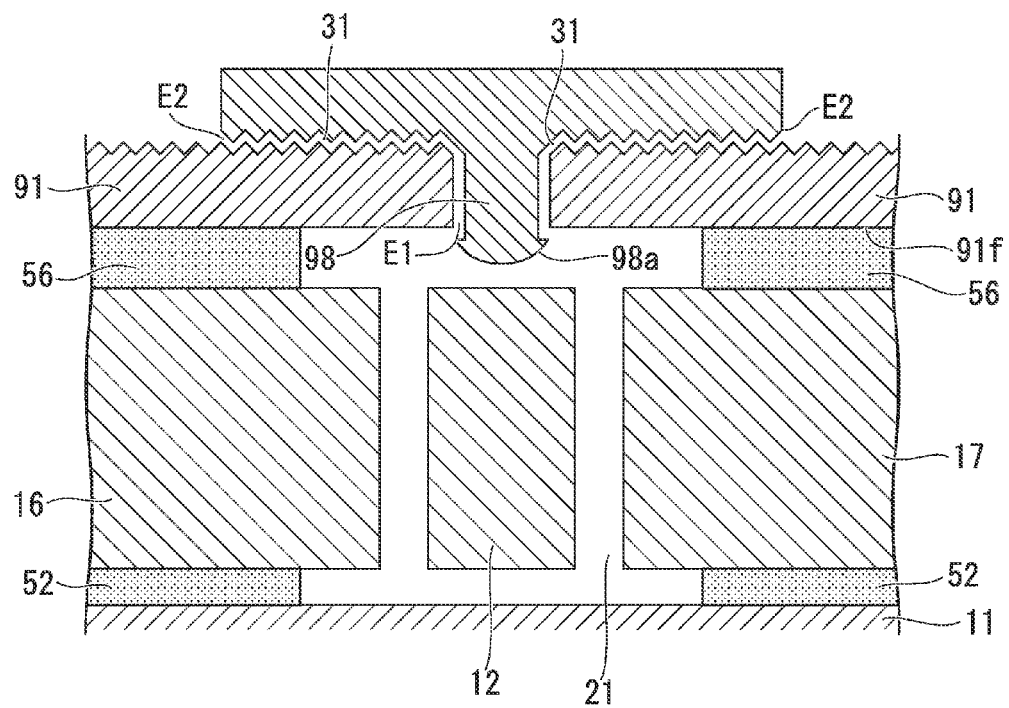
FIG. 29 is a sectional view illustrating the resonant transducer for describing a manufacturing method of the resonant transducer of the third embodiment.

Next, as shown in FIG. 29, a whole of the oxide layer 96, the insulated layer 56 around the resonator 12, and the oxidized layer 52 around the resonator 12 are removed by etching with dilute HF solution. By the process, the chamber 21 is formed around the resonator 12, and the gap around the resonator 12 is kept.

On the other hand, by removing the oxide layer 96 formed between the first polysilicon layer 91 and the second polysilicon layer 97, the gap 31 is formed between the first polysilicon layer 91 and the second polysilicon layer 97. The gap 31 extends from a first gap E1 between the first polysilicon layer 91 and the projection 98 to a second gap E2 between the first polysilicon layer 91 and the second polysilicon layer 97. The first gap E1 is communicated with the second gap E2. The dilute HF solution flows into the chamber 21 and flows from the chamber 21 via the gap 31 to form the chamber 21.

By the manufacturing method of the resonant transducer, even if a little waste solution remains between the resonator 12 and the first polysilicon layer 91 and the meniscus force of the waste solution bends the resonator 12 widely toward the first polysilicon layer 91, the resonator 12 comes into contact with the end face 98a of the projection 98 projecting into the chamber 21. Therefore, it is preventable that the resonator 12 adheres to the first polysilicon layer 91.

Further, in the manufacturing method of the third embodiment, as a cross-section shape of the end face 98a of the projection 98 is semicircle, a contact area of the projection 98 and the resonator 12 is very small. Therefore, as the resonator 12 does not adhere to the end face 98a of the projection 98, it is preventable that the resonator 12 becomes deformed.

While preferred embodiments of the invention have been described and illustrated above, it should be understood that these are exemplary of the invention and are not to be considered as limiting. Additions, omissions, substitutions, and other modifications can be made without departing from the scope of the present invention. Accordingly, the invention is not to be considered as being limited by the foregoing description, and is only limited by the scope of the appended claims.

What is claimed is:

1. A resonant transducer comprising:
  a silicon single crystal substrate;
  a silicon single crystal resonator disposed over the silicon single crystal substrate;
  a shell made of silicon, surrounding the resonator with a gap, and forming a chamber together with the silicon single crystal substrate;
  an exciting module configured to excite the resonator;
  a vibration detecting module configured to detect vibration of the resonator;
  a first layer disposed over the chamber, the first layer having a through-hole;
  a second layer disposed over the first layer;

a third layer covering the first layer and the second layer;
a projection extending from the second layer toward the resonator, the projection being spatially separated from the resonator, the projection being separated from the first layer by a first gap, the second layer being separated from the first layer by a second gap, the first gap is communicated with the second gap;
wherein the projection is disposed immediately above the resonator, and
a distance between the projection and the resonator is shorter than a distance between the first layer and the resonator and an end face of the projection is narrower than a width of the resonator.

2. The resonant transducer according to claim 1, wherein the first layer, the second layer, and the third layer are made of any one of polysilicon, amorphous silicon, SiC, SiGe, and Ge.

3. The resonant transducer according to claim 1, further comprising:
a non-empty spacer forming the second gap, the non-empty spacer being integral with the second layer.

4. The resonant transducer according to claim 1, wherein the through-hole is cuboid-shaped space extending along a longitudinal direction of the resonator, and
a part of the gap is rectangular-section cylindrical between an outer surface of the projection and an inner surface of the through-hole.

5. The resonant transducer according to claim 1, wherein a shape of the through-hole is oval or ellipse disposed along the longitudinal direction of the resonator, and
a part of the gap is cylindrical between an outer surface of the projection and an inner surface of the through-hole.

6. The resonant transducer according to claim 1, wherein pressure in the chamber is less than atmospheric pressure.

* * * * *